US008859492B2

(12) United States Patent  
Cowan et al.

(10) Patent No.: US 8,859,492 B2
(45) Date of Patent: Oct. 14, 2014

(54) METALLODRUGS HAVING IMPROVED PHARMACOLOGICAL PROPERTIES, AND METHODS OF MANUFACTURE AND USE THEREOF

(75) Inventors: James A. Cowan, Delaware, OH (US); Ada S. Cowan, Delaware, OH (US); Donna T. Palmer, San Diego, CA (US)

(73) Assignee: MetalloPharm, LLC, Delaware, OH (US)

( * ) Notice: Subject to any disclaimer, the term of this patent is extended or adjusted under 35 U.S.C. 154(b) by 0 days.

(21) Appl. No.: 13/470,299

(22) Filed: May 12, 2012

(65) Prior Publication Data

US 2012/0289454 A1 Nov. 15, 2012

Related U.S. Application Data

(60) Provisional application No. 61/485,528, filed on May 12, 2011.

(51) Int. Cl.

| | | |
|---|---|---|
| *C07K 19/00* | (2006.01) | |
| *C07K 7/08* | (2006.01) | |
| *C07K 14/46* | (2006.01) | |
| *C07K 2/00* | (2006.01) | |
| *A61K 38/05* | (2006.01) | |
| *A61K 38/10* | (2006.01) | |
| *A61K 38/17* | (2006.01) | |
| *A61K 38/08* | (2006.01) | |
| *A61P 31/00* | (2006.01) | |
| *C07K 5/068* | (2006.01) | |
| *C07K 1/113* | (2006.01) | |
| *A61K 47/48* | (2006.01) | |
| *C07K 7/06* | (2006.01) | |
| *C07K 5/02* | (2006.01) | |
| *C07H 23/00* | (2006.01) | |
| *A61K 38/00* | (2006.01) | |

(52) U.S. Cl.
CPC ............ *C07H 23/00* (2013.01); *C07K 2319/20* (2013.01); *A61K 47/48076* (2013.01); *C07K 7/06* (2013.01); *C07K 5/022* (2013.01); *A61K 38/00* (2013.01); *C07K 2319/70* (2013.01)
USPC ........... 514/2.3; 514/1.1; 514/21.3; 514/21.4; 514/21.5; 514/21.6; 514/21.7; 514/21.8; 530/324; 530/329; 530/322; 530/345; 530/300; 530/326; 530/328; 536/55; 540/474; 548/402; 548/533

(58) Field of Classification Search
CPC ......... A61K 38/00; A61K 38/05; C07K 1/113
See application file for complete search history.

(56) References Cited

U.S. PATENT DOCUMENTS

| | | |
|---|---|---|
| 3,994,966 A | 11/1976 | Sundberg et al. |
| 5,057,302 A | 10/1991 | Johnson et al. |
| 5,326,856 A | 7/1994 | Coughlin et al. |
| 5,480,970 A | 1/1996 | Pollak et al. |
| 5,571,698 A | 11/1996 | Ladner et al. |
| 5,631,146 A | 5/1997 | Szostak et al. |
| 5,691,145 A | 11/1997 | Pitner et al. |
| 5,888,530 A | 3/1999 | Netti et al. |
| 6,004,531 A | 12/1999 | Archer et al. |
| 6,057,098 A | 5/2000 | Buechler et al. |
| 6,403,777 B1 | 6/2002 | Cowan |
| 7,635,762 B2 | 12/2009 | Cook et al. |
| 2006/0019942 A1 | 1/2006 | Meggers et al. |
| 2008/0188422 A1 | 8/2008 | Cowan et al. |
| 2008/0213172 A1 | 9/2008 | Babich et al. |

FOREIGN PATENT DOCUMENTS

| | | | | |
|---|---|---|---|---|
| WO | WO 00/36136 | * | 6/2000 | ............. C12Q 1/100 |
| WO | 2005117997 A1 | | 12/2005 | |

OTHER PUBLICATIONS

Cowan JA. Catalytic metallodrugs. Pure Appl. Chem., vol. 80, No. 8, pp. 1799-1810, 2008.*
Butler A. Acquisition and utilization of transition metal ions by marine organisms. Science. Jul. 10, 1998;281(5374):207-10.*
Veronese FM. Peptide and protein PEGylation: a review of problems and solutions. Biomaterials 22 (2001) 405-417.*
Fang et al. Diastereoselective DNA cleavage recognition by Ni(II) x Gly-Gly-His-derived metallopeptides. J Am Chem Soc. Mar. 15, 2006; 128(10): 3198-3207.*
Gokhale et al. Metallopeptide-promoted inactivation of angiotensin-converting enzyme and endothelin-converting enzyme 1: toward dual-action therapeutics. J Biol Inorg Chem (2006) 11:937-947.*
Al-Obeidi, Peptide and Peptidomimetic Libraries. Molecular diversity and drug design. Mol Biotechnol. Jun. 1998;9(3):205-223.
Altman et al., Bifunctional Chelating Agents. Part 1.1-(p-Aminophenethyl)-ethylenediaminetetra-acetic Acid. J Chem Soc Perkin Trans I, 1983;365-368.
Altman et al., Bifunctional Chelating Agents. Part 2. Synthesis of 1-(2-Carboxyethyl)ethylenediaminetetra-acetic Acid by Ring Cleavage of a Substituted Imidazole. J Chem Soc Perkin Trans I. 1984:59-62.
Amstutz et al., In vitro display technologies: novel developments and applications. Curr Opin Biotechnol. Aug. 2001;12(4):400-405.
Blum et al., Isolation of peptide aptamers that inhibit intracellular processes. Proc Natl Acad Sci. Feb. 29, 2000;97(5):2241-2246.
Bourdon et al., Affinity Labeling of Lysine-149 in the Anion-Binding Exosite of Human alpha-Thrombin with an Nalpha-(Dinitrofluorobenzyl)hirudin C-Terminal Peptide. Biochemistry Jul. 10, 1990;29(27):6379-6384.

(Continued)

*Primary Examiner* — Karlheinz R Skowronek
*Assistant Examiner* — Jia-Hai Lee
(74) *Attorney, Agent, or Firm* — Michael A. Whittaker; Acuity Law Group

(57) ABSTRACT

It is an object of the present invention to provide improved pharmacological properties to molecules which bind to a target with low affinity (hereinafter referred to as a "ligand moiety") through linkage of such molecules to a metal binding moiety, thereby generating a combination molecule commonly referred to as a "metallodrug" or "metallotherapeutic." The metal binding domain of metallodrugs typically catalyzes oxido-reductase chemistry or acts as a Lewis-Acid catalyst, resulting in modification of proteins and nucleic acids that are in close proximity due to binding of the ligand moiety to its target.

44 Claims, 7 Drawing Sheets

(56) References Cited

OTHER PUBLICATIONS

Bradford and Cowan, Catalytic metallodrugs targeting HCV IRES RNA. Chem Commun (Camb), Mar. 25, 2012;48(25):3118-3120.
Brechbiel et al., Synthesis of 1-(p-Isothiocyanatobenzyl) Derivatives of DTPA and EDTA. Antibody Labeling and Tumor-Imaging Studies. Inorg Chem. 1986;25:2772-2781.
Brenner et al., Encoded combinatorial chemistry. Proc Natl Acad Sci USA. Jun. 15, 1992:89(12):5381-5383.
Carell et al., New promise in combinatorial chemistry: synthesis, characterization, and screening of small-molecule libraries in solution. Chem Biol. Mar. 1995;2(3):171-183.
Clark and Remcho, Aptamers as analytical reagents. Electrophoresis May 2002; 23(9):1335-1340.
Coe and Storer, Solution-phase combinatorial chemistry. Mol Divers. 1998-1999;4(1):31-38.
Colas et al., Targeted modification and transportation of cellular proteins. Proc Natl Acad Sci., Dec. 5, 2000;97(25):13720-13725.
Connell et al., Three Small Ribooligonucleotides with Specific Arginine Sites. Biochemistry Jun. 1, 1993;32(21):5497-5502.
Cox et al., Automated selection of aptamers against protein targets translated in vitro: from gene to aptamer. Nucleic Acids Res. Oct. 15, 2002;30(20):e108.
Cwirla et al., Peptides on phage: A vast library of peptides for identifying ligands. Proc Natl Acad Sci USA Aug. 1990;87(16):6378-6382.
Devlin et al., Random Peptide Libraries: A Source of Specific Protein Binding Molecules. Science Jul. 27, 1990;249(4967):404-406.
Dolle and Nelson, Comprehensive Survey of Combinatorial Library Synthesis: 1998. J Comb Chem. Jul.-Aug. 1999;1(4):235-282.
Enjalbal et al., Mass Spectrometry in Combinatorial Chemistry. Mass Spectrom Rev. May-Jun. 2000;19(3):139-161.
Famulok et al., Nucleic Acid Aptamers—From Selection in Vitro to Applications in Vivo. Acc Chem Res. Sep. 2000;33(9):591-599.
Felder, The Challenge of Preparing and Testing Combinatorial Compound Libraries in the Fast Lane, at the Front End of Drug Development. Chimia 1994:48:531-541.
Freidinger., Nonpeptidic ligands for peptide and protein receptors. Curr Opin Chem Biol. Aug. 1999;3(4):395-406.
Gallop et al., Applications of Combinatorial Technologies to Drug Discovery. 1. Background and Peptide Combinatorial Libraries. J Med Chem. Apr. 29, 1994;37(9):1233-1251.
Gokhale and Cowan, Inactivation of human angiotensin converting enzyme by copper peptide complexes containing ATCUN motifs. Chem Commun (Camb) Dec. 21, 2005;(47):5916-5918.
Gokhale and Cowan, Metallopeptide-promoted inactivation of angiotensin-converting enzme and endothelin-converting enzyme 1: toward dual-action therapeutics. J Biol Inorg Chem Oct. 2006;11(7):937-947.
Gokhale et al., Catalytic Inactivation of Human Carbonic Anhydrase I by a Metallopeptide-Sulfonamide Conjugate is Mediated by Oxidation of Active Site Residues. J Am Chem Soc. Feb. 27, 2008;130(8):2388-2389.
Gokhale et al., Stimulation and oxidative catalytic inactivation of thermolysin by copper•Cys-Gly-His-Lys. J Biol Inorg Chem Sep. 2007;12(7):981-987.
Gold, et al., Diversity of Oligonucleotide Functions. Annu Rev Biochem. 1995;64:763-797.
Gold, Oligonucleotides as Research, Diagnostic, and Therapeutic Agents. J Biol Chem. Jun. 9, 1995;270 (23):13581-13584.
Gordon et al., Applications of Combinatorial Technologies to Drug Discovery. 2. Combinatorial Organic Synthesis, Library Screening Strategies, and Future Directions. J Med Chem. May 13, 1994;37(10):1385-1401.
Gram, Phage display in proteolysis and signal transduction. Comb Chem High Throughput Screen. Feb. 1999;2 (1):19-28.
Gravert and Janda, Synthesis on soluble polymers: new reactions and the construction of small molecules. Curr Opin Chem Biol. Jun. 1997;1(1):107-113.

Green et al., Evaluation of PLED as a Chelating Ligand in the Preparation of Gallium and Indium Radiopharmaceuticals. Int J Nucl Med Biol. 1985;12(5):381-386.
Hanes and Pluckthun, In vitro selection and evolution of functional proteins by using ribosome display. Proc Natl Acad Sci. May 13, 1997;94(10):4937-4942.
Hocharoen and Cowan, Metallotherapeutics: Novel Strategies in Drug Design. Chemistry Sep. 7, 2009;15 (35):8670-8676.
Hohsaka and Sisido, Incorporation of non-natural amino acids into proteins. Curr Opin Chem Biol. Dec. 2002;6 (6):809-815.
Houghten et al., Generation and use of synthetic peptide combinatorial libraries for basic research and drug discovery. Nature Nov. 7, 1991;354(6348):84-86.
Houghten, Parallel Array and Mixture-Based Synthetic Combinatorial Chemistry: Tools for the Next Millennium. Annu Rev Pharmacol Toxicol. 2000;40:273-282.
Houghten, Peptide libraries: criteria and trends. Trends Genet. Jul. 1993:9(7):235-239.
James, Nucleic acid and polypeptide aptamers: a powerful approach to ligand discovery. Curr Opin Pharmacol. Oct. 2001;1(5):540-546.
Jayasena, Aptamers: An Emerging Class of Molecules That Rival Antibodies in Diagnostics. Clin Chem. Sep. 1999;45(9):1628-1650.
Jermutus et al., Ligand binding of a ribosome-displayed protein detected in solution at the single molecule level by fluorescence correlation spectroscopy. Eur Biophys J. Jun. 2002;31(3):179-184.
Jermutus et al., Recent advances in producing and selecting functional proteins by using cell-free translation. Curr Opin Biotechnol. Oct. 1998;9(5):534-548.
Jiang et al., Specific Aptamer-Protein Interaction Studied by Atomic Force Microscopy. Anal Chem. May 1, 2003;75(9):2112-2116.
Jin and Cowan, DNA Cleavage by Copper-ATCUN Complexes. Factors Influencing Cleavage Mechanism and Linearization of dsDNA. J Am Chem Soc. Jun. 15, 2005;127(23):8408-8415.
Jin and Cowan, Targeted Cleavage of HIV Rev Response Element RNA by Metallopeptide Complexes. J Am Chem Soc. Jan. 18, 2006;128(2):410-411.
Jin et al., Influence of Stereochemistry and Redox Potentials on the Single- and Double-Strand DNA Cleavage Efficiency of Cu(II) and Ni(II) Lys-Gly-His-Derived ATCUN Metallopeptides. J Am Chem Soc. Jul. 4, 2007;129 (26):8353-8361.
Joyner and Cowan, Targeted Cleavage of HIV RRE RNA by Rev-Coupled Transition Metal Chelates. J Am Chem Soc. Jun. 29, 2011;133(25):9912-9922.
Joyner et al., Factors Influencing the DNA Nuclease Activity of Iron, Cobalt, Nickel, and Copper Chelates. J Am Chem Soc. Oct. 5, 2011;133(39):15613-15626.
Joyner et al., Targeted Catalytic Inactivation of Angiotensin Converting Enzyme by Lisinopril-Coupled Transition-Metal Chelates. J Am Chem Soc. Feb. 22, 2012;134(7): 3396-3410.
Anand et al., Toward the development of a potent ahd selective organoruthenium mammalian sterile 20 kinase inhibitor. J Med Chem. Mar. 2009;52(6):1602-1611.
International Search Report and Written Opinion issued in PCT/US2012/037678 dated Nov. 5, 2012.
Dougan et al., Catalytic organometallic anticancer complexes. Proc Natl Acad Sci USA Aug. 19, 2008;105(33):11628-11633.
Thamapipol et al., Chiral Ruthenium Lewis Acid Catalyzed Intramolecular Diets-Alder Reactions. Org Lett. Dec. 17, 2010;12(24):5604-5607.
Jung et al., Selection for Improved Protein Stability by Phage Display. J Mol Biol. Nov. 19, 1999;294(1):163-180.
Kim and Kahn, A Merger of Rational Drug Design and Combinatorial Chemistry: Development and Application of Peptide Secondary Structure Mimetics. Comb Chem High Throughput Screen. Jun. 2000;3(3):167-183.
Kopylov and Spiridonova, Combinatorial Chemistry of Nucleic Acids: SELEX. Mol Biol (Mosk). Nov.-Dec. 2000;34(6):1097-1113.
Krebber et al., Selectively-infective Phage (SIP): A Mechanistic Dissection of a Novel in vivo Selection for Protein-Ligand Interactions. J Mol Biol. May 9, 1997;268(3):607-618.

(56) References Cited

OTHER PUBLICATIONS

Kroll et al., Excretion of Yttrium and Lanthanum Chelates of Cyclohexane 1,2-Trans Diamine Tetraacetic Acid and Diethylenetriamine Pentaacetic Acid in Man. Nature Nov. 2, 1957;180(4592):919-920.
Kundu et al., Combinatorial chemistry: Polymer supported synthesis of peptide and non-peptide libraries. Prog Drug Res. 1999;53:89-156.
Lam et al., A new type of synthetic peptide library for identifying ligand-binding activity. Nature Nov. 7, 1991;354(6348):82-84.
Lebl et al., One-Bead-One-Structure Combinatorial Libraries. Biopolymers 1995;37(3):177-198.
Long, Ni(II) Xaa-Xaa-His Metallopeptide-DNA/RNA Interactions. Accounts of Chemical Research Oct. 1999;32(10):827-836.
Lytle et al., Domains on the hepatitis C virus internal ribosome entry site for 40s subunit binding. RNA Aug. 2002;8(8):1045-1055.
Madden et al., Synthetic combinatorial libraries: Views on techniques and their application. Perspectives in Drug Discovery and Design 1994;2:269-285.
Meares and Goodwin, Linking Radiometals to Proteins with Bifunctional Chelating Agents. J Protein Chem. 1984;3(2):215-228.
Menger et al., Application of Aptamers in Therapeutics and for Small-Molecule Detection. Handb Exp Pharmacal. 2006;(173):359-373.
Merritt, Solution phase combinatorial chemistry. Comb Chem High Throughput Screen. Jun. 1998;1(2):57-72.
Michael et al., Metal binding and folding properties of a minimalist Cys2His2 zinc finger peptide. Proc Nati Acad Sci USA. Jun. 1, 1992;89(11):4796-4800.
Moi et al., Copper Chelates as Probes of Biological Systems: Stable Copper Complexes with a Macrocyclic Bifunctional Chelating Agent. Anal Biochem. Jul. 1985;148:249-253.
Nelson and Griswold, A computer program for calculating antibody affinity constants. Comput Methods Programs Biomed. Jul.-Aug. 1988;27(1):65-68.
Perrin, Nucleic Acids for Recognition and Catalysis: Landmarks, Limitations, and Looking to the Future. Comb Chem High Throughput Screen. Jun. 2000;3(3):243-269.
Pluckthun et al., In Vitro Selection and Evolution of Proteins. Adv Protein Chem. 2000;55:367-403.
Raffler et al., A Novel Class of Small Functional Peptides that Bind and Inhibit Human alpha-Thrombin Isolated by mRNA Display. Biol. Jan. 2003;10(1):69-79.
Roberts and Szostak, RNA-peptide fusions for the in vitro selection of peptides and proteins. Proc Natl Acad Sci. Nov. 11, 1997;94(23):12297-12302.
Schweizer and Hindsgaul, Combinatorial synthesis of carbohydrates. Curr Opin Chem Biol Jun. 1999;3(3):291-298.
Scott and Smith, Searching for Peptide Ligands with an Epitope Library. Science Jul. 27, 1990;249(4967):386-390.
Sieber et al., Selecting proteins with improved stability by a phage-based method. Nat Biotechnol. Oct. 1998;16(10):955-960.
Spada et al., Selectively Infective Phages (SIP). Biol Chem. Jun. 1997;378(6):445-456.
Sun, Recent advances in liquid-phase combinatorial chemistry. Comb Chem High Throughput Screen. Dec. 1999;2(6):299-318.
Sundberg, et al., Selective Binding of Metal Ions to Macromolecules Using Bifunctional Analogs of EDTA. J Med Chem. Dec. 1974;17(12):1304-1307.
Tahiri-Alaoui et al., High affinity nucleic acid aptamers for streptavidin incorporated into bi-specific capture ligands. Nucleic Acids Res. May 15, 2002;30(10):e45.
Taliaferro et al., New Multidentate Ligands. 22. N,N'-Dipyridoxylethylenediamine-N,N'-diacetic Acid: A New Chelating Ligand for Trivalent Metal Ions. Inorg Chem. 1984;23:1188-1192.
Van Erp et al., Application of a Sol Particle Immunoassay to the Determination of Affinity Constants of Monoclonal Antibodies. J Immunoassay 1991;12(3):425-443.
Wang et al., A DNA Aptamer Which Binds to and Inhibits Thrombin Exhibits a New Structural Motif for DNA. Biochemistry Mar. 2, 1993;32(8):1899-1904.
Ward et al., Binding activities of a repertoire of single immunoglobulin variable domains secreted from *Escherichia coli*. Nature Oct. 12, 1989;341(6242):544-546.
Wessjohann, Synthesis of natural-product-based compound libraries. Curr Opin Chem Biol. Jun. 2000;4(3):303-309.
Wilson and Szostak, In vitro selection of functional nucleic acids. Ann Rev Biochem. 1999;68:611-47.
Wilson et al., Simplified conjugation chemistry for coupling peptides to F(ab') fragments: autologous red cell agglutination assay for HIV-1 antibodies. J Immunol Methods Oct. 14, 1994;175(2):267-273.
Wlotzka et al., In vivo properties of an anti-GnRH Spiegelmer: an example of an oligonucleotide-based therapeutic substance class. Proc Natl Acad Sci USA Jun. 25, 2002;99(13):8898-8902.
Yarmush, Coupling of antibody-binding fragments to solid-phase supports: site-directed binding of F(ab')2 fragments. J Biochem Biophys Methods Dec. 1992;25(4):285-297.
Lacolurciere et al., "Mechanism of Neomycin and Rev Peptide Binding to the Rev Responsive Element of HIV-1 as Determined by Fluorescence and NMR Spectroscopy", Biochemisty, 2000, 39:5630-5641.
Van Ryk et al., "Real-time Kinetics of HIV-1 Rev-Rev Response Element Interactions", The Journal of Biological Chemistry, 1999, 274(25):17465-17463.

\* cited by examiner

METALLODRUGS HAVING IMPROVED PHARMACOLOGICAL PROPERTIES, AND METHODS OF MANUFACTURE AND USE THEREOF

The present application claims priority to U.S. Provisional Patent Application 61/485,528 filed May 12, 2011, which is hereby incorporated by reference in its entirety, including all tables, figures, and claims.

SEQUENCE LISTING

The instant application contains a Sequence Listing which has been submitted in ASCII format via EFS-Web and is hereby incorporated by reference in its entirety. Said ASCII copy, created on Jun. 14, 2012, is named MET001UT.txt and is 33,077 bytes in size.

BACKGROUND OF THE INVENTION

The following discussion of the background of the invention is merely provided to aid the reader in understanding the invention and is not admitted to describe or constitute prior art to the present invention.

A common starting point in drug development is the identification through screening or rational design of compounds that bind or exhibit some inhibitory activity against their intended targets. Because of the theoretically large chemical space of drug-like compounds, the "hit rate" of such approaches can be relatively low. In addition, many "hits" bind to the intended drug target with lower affinities than useful. Often, the lead compounds identified bind to their targets with micromolar and sometimes weaker affinities. To become effective drugs, the binding affinities of those compounds need to be optimized by three or more orders of magnitude. As a consequence, more effort has to be spent on optimization to obtain lead compounds with an acceptable affinity.

This task is not a trivial one if one considers that it may have to be done while satisfying several other stringent constraints, e.g., the molecular mass cannot substantially exceed 500 Da in order for the molecule to be orally bioavailable; the compound should exhibit appropriate target selectivity, appropriate membrane permeability and sufficient water solubility; the compound should exhibit an adequate pharmacokinetic profile, no toxicity, and so forth. These constraints considerably reduce the universe of chemical functionalities that can be utilized to achieve the optimization goals. The result is often that low affinity lead compounds having unique properties become abandoned during the drug development process.

These affinity limitations are not unique to small molecule drug compounds. Many of the antibody-based drugs presently used in clinically exhibit affinities in the nanomolar to picomolar range; however, the combinatorial phage display methods used to generate lead compounds often rely on naive immunoglobulin libraries which lack the high affinity binders typically arising from antigen stimulation. The result is typically an antibody lead compound which requires rounds of affinity maturation in order to arrive at a successful drug.

As noted above, lead optimization strategies often result in the loss of promising drug candidates and high failure rates in drug discovery programs. There remains a need in the art for approaches to improving success rates in drug discovery.

SUMMARY OF THE INVENTION

It is an object of the present invention to provide improved pharmacological properties to molecules which bind to a target with low affinity (hereinafter referred to as a "ligand moiety") through linkage of such molecules to a metal binding moiety, thereby generating a combination molecule commonly referred to as a "metallodrug" or "metallotherapeutic." The metal binding domain of metallodrugs typically catalyzes oxido-reductase chemistry or acts as a Lewis-Acid catalyst, resulting in modification of proteins and nucleic acids that are in close proximity due to binding of the ligand moiety to its target.

In contrast to traditional drug discovery programs, in which candidate drugs display high affinity but reversible binding to a therapeutic target, high affinity binding of a ligand moiety is unnecessary, and even undesirable, according to the catalytic metallodrug concepts described herein.

In a first aspect, the present invention provides compositions for catalytically inactivating a biochemical target of interest, comprising:
a ligand moiety which binds to the biochemical target with an affinity of between about $10^4$ M$^{-1}$ and about $5 \times 10^8$ M$^{-1}$; and
a metal binding moiety,
wherein the ligand moiety and the metal binding moiety are covalently linked.

In a related aspect, the present invention provides compositions for catalytically inactivating a biochemical target of interest, comprising:
a ligand moiety which binds to the biochemical target; and
a metal binding moiety,
wherein the ligand moiety and the metal binding moiety are covalently linked, and wherein the ligand moiety optimally binds to its biochemical target with a $k_{off}$ that is at least similar to the rate constant for the inactivation chemistry ($k_{cat}$) of the metal binding moiety.

In certain embodiments, the metal binding moiety comprises a metal bound thereto, wherein said metal is redox-active in the bound state under oxidative conditions to generate one or more reactive oxygen species and/or the metal binding moiety has a metal bound thereto, wherein said metal is active as a Lewis acid catalyst in the bound state under hydrolytic conditions.

In various embodiments, the metal bound to the metal binding moiety is a cation of a metal selected from the group consisting of an alkaline earth metals, metals which give rise to cations with an incomplete d sub-shell, lanthanide and actinide metals. In preferred embodiments, the transition metal is selected from the group consisting of Cu(II), Cu(III), Ni(II), Ni(III), Zn(II), Fe(II), Fe(III), Co(II), Co(III), Cr(II), and Cr(III).

The ligand moieties of the present invention may be any molecular functionality which binds to a desired biochemical target with the desired kinetic properties; specifically, prefers $k_{off}$ values that are at least similar to the rate constant for the inactivation chemistry ($k_{cat}$). In certain embodiments, an affinity of a ligand moiety for its target is between about $10^4$ M$^{-1}$ and about $5 \times 10^8$ M$^{-1}$. Such molecular functionalities will typically comprise an organic motif. In specific embodiments, the molecular functionality comprises one or more of a peptide backbone, a carbohydrate backbone, or a nucleic acid backbone. Exemplary molecules are secondary metabolites, antibodies, protein nucleic acids, aptamers, oligonucleotides, ribozymes, siRNAs, naturally occurring ligand moieties for cellular receptors, etc. This list is not meant to be limiting. In preferred embodiments, the ligand moiety comprises an organic molecular motif selected from the group consisting of an aptamer, a small organic molecule, a peptidomimetic, a dendrimer, an antibiotic, a secondary metabolite, and an antibody.

The metal binding moieties of the present invention may be any chemistry which binds a metal in a catalytically active conformation. In certain embodiments, the metal binding moiety comprises an organic chelating ligand such as those known in the art using amine and carboxylate functionalities on the organic chelating ligand. By way of example, such an organic chelating ligand preferably coordinates a metal using the coordination chemistry of a compound selected from the group consisting of diethylenetriaminepentaacetic acid (DTPA), ethylenediamine tetraacetic acid (EDTA), N,N-bis (carboxymethyl)glycine (NTA), diethylenetriaminepentaacetate (DTPA), 1,4,7,10-tetraazacyclododecane-1,4,7,10-tetraacetic acid (DOTA), Mercaptoacetylglycine (MAG3), 1,4,8,11-Tetraazacyclotetradecane (CYCLAM), 1,4,7,10-tetraazacyclododecane, cyclen, 1,4,7-triazacyclononane (TACN), and hydrazinonicotinamide (HYNIC).

The compositions of the present invention are active against a variety of biochemical targets, such as biochemical targets selected from the group consisting of a bacterial component, a viral component, a fungal component, a human cellular component, a protozoan component, a serum component, an extracellular matrix component, a cancer cell component, and a pathogen-derived toxin. By way of example, in certain embodiments the biochemical target is a cellular or serum component selected from the group consisting of a cell receptor, a cytokine, a hormone, an enzyme, and a misfolded or polymeric form of a naturally occurring molecule. A composition, when it is bound to the biochemical target, can bring the metal binding moiety within 20 nm of the biochemical target in order to improve the reaction kinetics of the metal catalyst.

In related aspects, the present invention provides methods for improving the efficacy of a current or candidate therapeutic molecule which is a ligand moiety to a biochemical target, comprising: covalently conjugating said current or candidate therapeutic molecule, which lacks a metal-binding domain, to a metal binding moiety, preferably wherein the current or candidate therapeutic molecule binds to its intended biochemical target with an affinity of between about $10^4 M^{-1}$ and about $5 \times 10^8 M^{-1}$ and/or binds to its intended biochemical target with a $k_{off}$ that optimally is at least similar to the rate constant for the inactivation chemistry ($k_{cat}$) of the metal binding moiety.

In other related aspects, the present invention provides methods for therapeutically inactivating a biochemical target, comprising:
administering to a subject in need thereof a composition according to the present invention under conditions wherein the composition binds to, and generates reactive oxygen species proximate to the biochemical target, wherein the concentration of reactive oxygen species generated conformationally and/or functionally alters the biochemical target to therapeutic effect.

In other related aspects, the present invention provides methods for therapeutically inactivating a biochemical target, comprising:
administering to a subject in need thereof a composition according to the present invention under conditions wherein the composition binds to, and is active as a Lewis acid catalyst proximate to the biochemical target, wherein the concentration of reactive species generated conformationally and/or functionally alters the biochemical target to therapeutic effect.

BRIEF DESCRIPTION OF THE FIGURES

FIG. 5 discloses "M-KGHK" as SEQ ID NO: 106.

Figure 1:
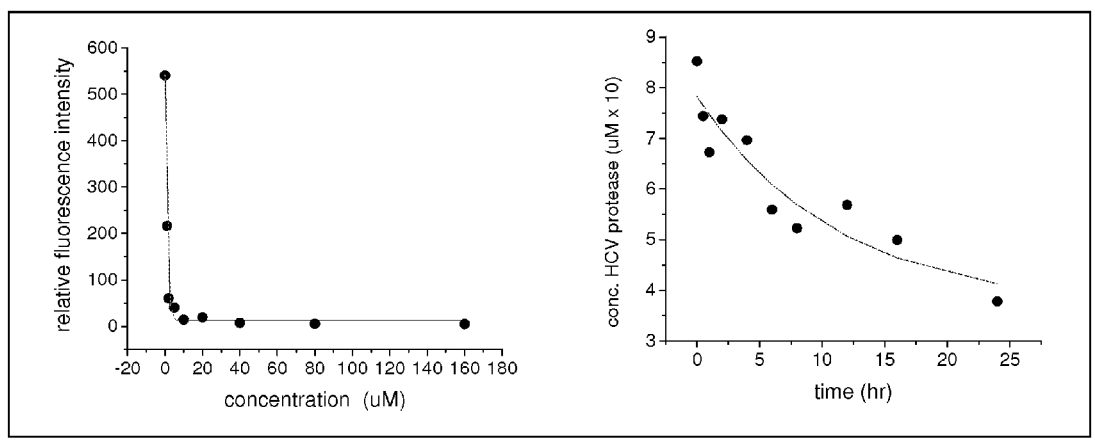
FIG. 1: (left) The Cu-GGHGDeLI(Cha)C complex shows relatively high affinity binding to the HCV protease ($K_1$~500 nM), but (right) the catalytic efficiency is poor, with rate constant for inactivation $k_{inact} < 0.083\ h^{-1}$ in the presence of ascorbate/$O_2$ and most likely reflecting the rate-limiting release of catalyst from the modified inactivated protease.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

The present invention relates to metallodrugs that combine a metal binding moiety and ligand moiety. By means of a metal species bound thereto, such metallodrugs catalytically degrade or inactivate a desired target entity through the use of a metal catalyst component of the metallodrug. The inclusion of a ligand moiety permits preferential delivery of the metallodrug to a desired target biomolecule. Such metallodrugs may target both nucleic acid and protein biomolecules, and may be used in pharmaceutical compositions for therapeutic and prophylactic purposes. Typically, nucleic acid targets are subject to strand scission chemistry mediated by ribose H-atom abstraction, while proteins are inactivated either through oxidative damage, or by backbone hydrolysis or oxidative scission.

By careful selection of the affinity of the metallodrug for its target biomolecule, an improved efficiency of catalytic inactivation of the target can be achieved. This stems from the relationship between affinity and the on/off rate constants for binding ($K_{assoc} = k_{on}/k_{off}$). Higher affinity binding to a target biomolecule, which is believed in the art to be preferable for drug compounds, is promoted by larger $k_{on}$ and/or smaller $k_{off}$ values. By contrast, the present invention demonstrates that efficient catalytic turnover optimally requires $k_{off}$ values that are at least similar to the rate constant for the inactivation chemistry ($k_{cat}$), to ensure the availability of metallodrug catalyst for new target molecules, and will be best promoted by relatively high values for both $k_{on}$ and $k_{off}$. This will result in weaker $K_{assoc}$ values. Contrary to the teachings in the art, those metallodrugs with weaker binding affinity can, in fact, promote more efficient inactivation of the target biomolecule, consistent with the more rapid release of metallodrug catalyst from the target following modification of the target. Furthermore, binding to off-target molecules can be better tolerated, as the metallodrugs of the present invention gain selectivity both through binding affinity coupled with successful position of the metal-binding ligand to its intended inactivation target.

DEFINITIONS

"Administration" as it applies to a human, mammal, mammalian subject, animal, veterinary subject, placebo subject, research subject, experimental subject, cell, tissue, organ, or biological fluid, refers without limitation to contact of an exogenous ligand moiety, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

By "purified" and "isolated" is meant, when referring to PPS fraction, that a specific molecular weight range accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the PPS present invention. The weights of water, buffers, salts, detergents, reductants, protease inhibitors, stabilizers (including an added protein such as albumin), and excipients, and molecules having a molecular weight of less than 1000, are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof, that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $5 \times 10^8$ $M^{-1}$. Affinity is calculated as $K_d = k_{off}/k_{on}$ ($k_{off}$ is the dissociation rate constant, $k_{on}$ is the association rate constant and $K_d$ is the equilibrium constant).

With respect to two kinetic constants such as $k_{cat}$ and $k_{off}$ the phrase "at least similar" refers to values +/−a factor of 10 of one another, and preferably +/−a factor of 5 of one another.

Affinity can be determined at equilibrium by measuring the fraction bound (r) of labeled ligand at various concentrations (c). The data are graphed using the Scatchard equation: r/c=K (n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_A$, n and ΔH. Note that $K_A = 1/K_d$.

The terms "sterilization" and "sterilize" as used herein refer to any process that eliminates (removes) or kills all or a portion of the microbes, and preferably all or a portion of the transmissible microbes (including, but not limited to, fungi, bacteria, viruses, spore forms, etc.) present on an inanimate object such as a surface, a fluid, a medication, or a medium such as biological culture media. "Surfaces" in this context include objects such as textiles, gloves, walls, countertops, etc.

The term "subject" as used herein refers to a human or non-human organism. Thus, the methods and compositions described herein are applicable to both human and veterinary disease, as well as sterilization of inanimate objects. In certain embodiments, subjects are "patients," i.e., living humans that are receiving medical care for a disease or condition. This includes persons with no defined illness who are being investigated for signs of pathology. Preferred are subjects who have an existing diagnosis of an inflammatory disease, sickle cell disease, bacterial disease, viral disease, cancer, atherosclerosis, peripheral arterial occlusive disease, an acute coronary syndrome, other cardiovascular disease, acute lung injury, systemic lupus erythematosus, or multiple sclerosis.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.). "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Metal Binding Moieties

Suitable metal binding domains are described, for example, in U.S. Pat. Nos. 5,057,302; 5,326,856; 5,480,970; 6,004,531, 6,403,777; and in International Publication WO05/117997, each of which is hereby incorporated in its entirety, including all tables, figures and claims. Metallodrugs of the present invention may be formed by coupling of a ligand moiety to a metal binding domain through the use of bifunctional chelating agents. Such chelating agents comprising an array of metal-binding groups plus a moiety capable of covalent binding to a protein substrate are known the art. Preferred are organic chelating groups which coordinate a metal using amine and carboxylate functionalities on the organic chelating group. Examples include compounds such as diethylenetriaminepentaacetic acid (DTPA), ethylenediamine tetraacetic acid (EDTA), N,N-bis(carboxymethyl)glycine (NTA), diethylenetriaminepentaacetate (DTPA), 1,4,7,10-tetraazacyclododecane-1,4,7,10-tetraacetic acid (DOTA), Mercaptoacetylglycine (MAG3), 1,4,8,11-Tetraazacyclotetradecane (CYCLAM), 1,4,7,10-tetraazacyclododecane, cyclen, 1,4,7-triazacyclononane (TACN), and hydrazinonicotinamide (HYNIC), and derivatives thereof.

Diethylenetriaminepentaacetic acid (DTPA) and its derivatives comprise a backbone of three nitrogen atoms linked by two ethylene chains. Extending from the nitrogen atoms on the backbone are five carboxymethyl moieties. Methods have been described whereby one of the carboxymethyl groups may be reacted to form an amide bond with an amino acid residue present on an antibody or other protein molecule. The other four carboxymethyl moieties, together with the three nitrogen atoms, then remain available for metal binding.

In order to avoid the potential for such undesired cross-linking, bifunctional chelating agents incorporating a unique protein substrate reactive site have been developed. Ethylenediaminetetraacetic acid (EDTA) and its derivatives comprise a backbone of two nitrogen atoms linked by an ethylene chain. Extending from the nitrogen atoms on the backbone are four carboxymethyl moieties which with the nitrogen atoms are suitable for metal. Bifunctional chelating derivatives of EDTA are characterized by the attachment of a unique reactive function at a methylene carbon of the polyamine backbone. Sundberg, et al., J. Med. Chem. 17, 1304 (1974) discloses the synthesis of an EDTA derivative bearing a para-aminophenyl protein reactive substituent. This derivative may in turn be converted to bifunctional chelating agents capable of being coupled to protein substrates under mild conditions either by reaction of the amine with a portion of a chemically modified protein or by treatment of the primary amine to form other substituents capable of binding to protein substrates under mild conditions.

Meares, et al., J. Protein Chem., 3, 215-228 (1984) discloses methods whereby the para-aminophenyl derivative is converted to a diazonium derivative through nitrous acid treatment, to an isothiocyanate derivated by treatment with thiophosgene, to a bromoacetamide derivative by treatment with bromoacetylbromide and to a palmitaamidobenzyl derivative by treatment with palmitoyl chloride. Altman, et al., J. Chem. Soc. Perkin Trans. I., 365, 59-62 (1983) discloses a number of phenethyl analogues of the above EDTA compounds. See also, Sundberg, et al., U.S. Pat. No. 3,994, 966.

Cyclic chelating agents are known in the art. Kroll, et al., Nature, 180 919-20 (1957) discloses the use of cyclohexane-1,2-trans-diaminetetraacetic acid for the removal of heavy metal ions from the human body. Moi, et al., Anal. Biochem., 148, 249-253 (1985) discloses a macrocyclic bifunctional chelating agent precursor named 6-(p-nitrobenzyl)-1,4,8,11-tetra-azacyclotetradecane N,N',N'',N'''-tetraacetic acid (p-nitrobenzyl-TETA) which forms a copper chelate which is extremely stable in human serum under physiological conditions. In addition, the p-bromoacetamidobenzyl derivative of TETA shows high stability after conjugation to a monoclonal antibody. The Moi, et al. reference also discloses that improved metal binding yields may be obtained in some cases where the conjugate contains a spacer group between the protein and TETA.

Also of use in the present invention are the disclosures of Green, et al., Int. J. Nucl. Med. Biol., 12, 381-85 (1985) and Taliaferro, et al., Inorg. Chem. 23 1188-92 (1984) disclosing chelating agents. Green, et al. discloses a sexadentate ligand N,N'-dipyridoxylethylenediamine-N,N'-diacetic acid (PLED) complexed with gallium68 and indium111. Taliaferro, et al., discloses PLED chelates as well as those of N,N'-ethylene-bis[2-(o-hydroxy phenyl)glycine] (EHPG) and N,N'-bis(2-hydroxybenzyl)ethylenediamine-N,N'-diacetic acid (HBED).

Other variations on known DTPA and EDTA derivatives include those of Brechbiel, et al., Inorg. Chem., 25, 2772-81 (1986) which discloses derivatives of DTPA wherein para-aminophenyl substituents are attached to the methylene carbons of the polyamine backbone. In addition, Altman, et al., J. Chem. Soc. Perkin Trans. I., 59 (1984) discloses a 2-carboxyethyl chelating derivative of EDTA.

In other examples, the metal binding domain may comprise an amino terminal Cu(II) and Ni(II) binding ("ATCUN") motif. The ATCUN motif comprises a peptide having (1) a free NH2-terminus, (2) two intervening peptide nitrogens, and (3) a histidine (H) residue at position 3. The ATCUN motif peptides are capable of binding metals such as Cu(II), Ni(II), Fe(III), Al(III), Co(II), and Co(III). Specific examples of ATCUN motifs include, but are not limited to, GGH, KGHK (SEQ ID NO: 2), VIHN (SEQ ID NO: 3), and YIHPF (SEQ ID NO: 4). FIG. 1 illustrates these specific ATCUN motifs with a metal M bound by the motif. In still another example—metal binding motif may lie internal to peptide sequence.

In still other examples, the metal binding domain may comprise the ATCUN motif having modifications with non-natural amino acids containing metal-binding groups. The modifications may be non-natural amino acids derived from modifications at the N- and C-termini of the ATCUN motif. For example cyclised lysines and pyridyl/pyrazolyl terminal secondary amino functionalities may be used.

Figure 2:
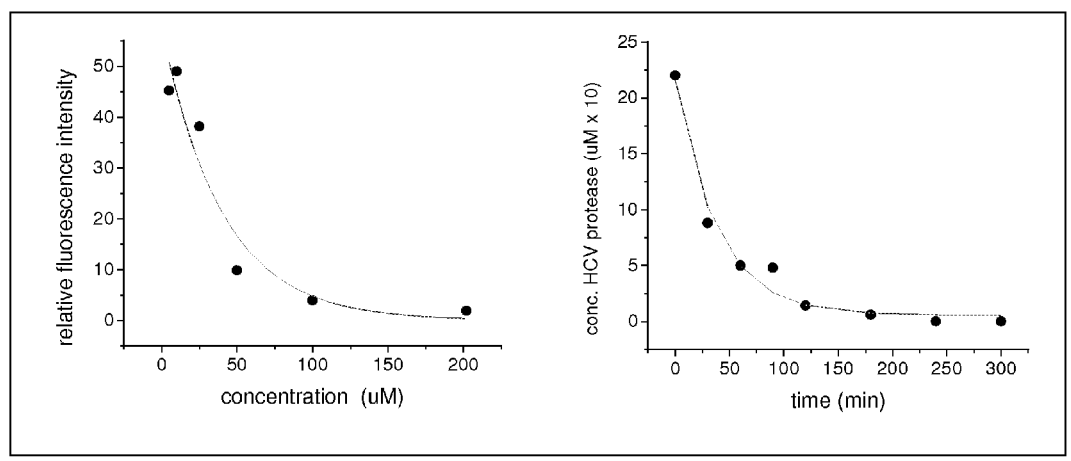
FIG. 2: (left) The Cu-GGHGDEMEEC complex (SEQ ID NO: 1) shows relatively low affinity binding to the HCV protease ($K_1$~48 μM), but (right) the catalytic efficiency is improved over that shown in FIG. 1, with rate constant for inactivation $k_{inact}$~1.6 $h^{-1}$ in the presence of ascorbate/O2 and consistent with the more rapid release of catalyst from the modified inactivated protease.
Figure 3:
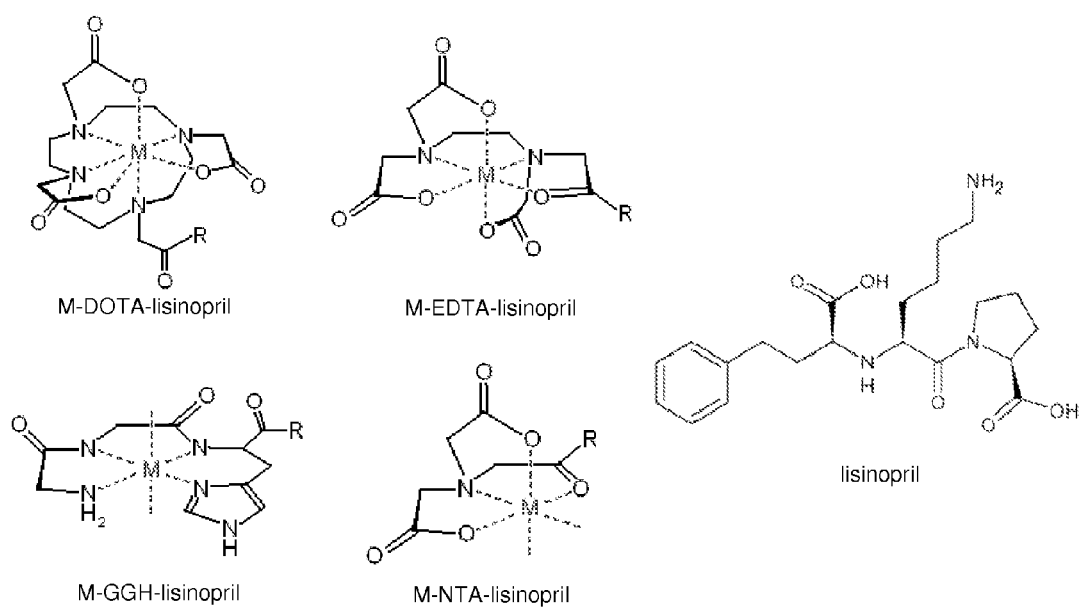
FIG. 3: Exemplary lisinopril metallodrugs of the present invention that target sACE-1.

In yet another example, the N-terminus of a peptide may have an ATCUN motif thereon. A suitable N-terminus modification is described in Current Opinion in Chemical Biology 2002, 6, 809-815. The C-terminus of a peptide may have an ATCUN motif thereon. An example of a scheme for such a metal binding domain is illustrated in FIG. 2. This type of metal binding domain is discussed in Bioconjugate Chem. 2000, 11, 762-771. Another suitable metal binding domain is a peptide having an ATCUN motif on an internal portion of the peptide. A scheme for preparing one such domain is illustrated in FIG. 3 and discussed in Accounts of Chemical Research 1999, 32(10), 827. It will be understood that the peptide may be any suitable peptide of any suitable length. It will be further understood that the ATCUN motif may be any suitable motif.

In another example, metal binding domains having an ATCUN motif may be modified to enhance metal reactivity. The N-terminus of the ATCUN motif may be modified to replace primary amino functionality with secondary amino function. For example, a Schiff base may be utilized. In addition point variations of one or more of the amino acids in the ATCUN motif may be made (except the His in the third position). For example, Xaa-G-H or G-Xaa-H may be used where Xaa represents any amino acid. In addition substitution of L- for D-configuration amino acids may be made for one or more of the amino acids in the ATCUN motif me. In both cases, such modifications may induce steric and electronic changes in the ATCUN motifs resulting in a modulation of metal reactivity.

In still other examples, the metal binding domain may comprise an octa-repeat motif from the prion protein having a sequence of PHGGGWGQ (SEQ ID NO: 5). In a further example, the metal binding domain may comprise a motif comprising histidine (H) as the first residue and glycine (G) as the third residue starting from the N-terminus of the motif. For example, the metal binding domain may comprise HGG, HGGG (SEQ ID NO: 6), HGGGG (SEQ ID NO: 7), HGGC (SEQ ID NO: 8), and the like. This domain may be repeated within a peptide sequence and cysteine (C) residues may be incorporated to increase metal binding affinity. It will be understood that the motif may comprise only a portion or portions of the metal binding domain. In another example, the metal binding domain may comprise a motif having histidine (H) as the third residue from the N-terminus. For example, the metal binding domain may comprise Xaa-Xaa-H with Xaa being any amino acid. The motif may be repeated in the metal binding domain, and the motif may comprise only a portion or portions of the metal binding domain. In one example, the metal binding domain may comprise a short peptide of less than about 30 amino acids containing a motif having H as the third residue and or a motif having H as the first residue and G as the third residue or having a motif of Xaa-H-Xaa-Gly-Xaa-anywhere within the sequence.

The metal binding domain may also comprise zinc finger peptides having a zinc binding unit comprising two cysteine (Cys) and two histidine (His) residues. One such suitable zinc finger peptide is Lys-Tyr-Ala-Cys-Ala-Ala-Cys-Ala-Ala-Ala-Phe-Ala-Ala-Lys-Ala-Ala-Leu-Ala-Ala-His-Ala-Ala-Ala-His-Ala-Lys (SEQ ID NO: 9) which is reported in Proc Natl Acad Sci USA. 1992 Jun. 1; 89(11):4796-800. The metal binding domain may comprise short peptide conjugates with small molecular weight synthetic metal binding motifs. The small molecular weight synthetic metal binding motif may be selected to bind a desired metal. For example, the synthetic metal binding motif may comprise cyclam, bipyridyl, terpyridine, porphyrin, and TREN (tris(2-aminoethyl)amine). The metal binding domain may comprise Xaa-Xaa-cyclam/bipyridyl and the like. Additionally, the metal binding domain may comprise a peptide mimic with metal binding abilities.

In another example the metal binding domain may be a cyclam chelating motif that is tagged to a targeting peptide.

The metal binding domain is preferably exposed to a desired metal so that the metal is bound to the metal binding domain and metal-ligand complexes may be formed. It will be understood that the metal binding domain may be exposed to the metal either before the formation of the conjugate with the targeting domain or after the formation of the conjugate. Any suitable metal may be used. Examples of suitable metals include transition metals such as Cu(II), Cu(III), Ni(II), Ni(III), Zn(II), Fe(II), Fe(III), Co(II), Co(III), Cr(II), and Cr(III), and other second and third row transition metal ions, and non-transition metals such as Al(III). The metal may be bound to the metal binding domain in any suitable manner. For example, a solution of 1 mM peptide in 10 mM Tris buffer (pH=7.4) may be mixed with 0.95 mM $CuCl_2$ in 10 mM Tris buffer solution in a 1:1 ratio. It will be understood that any other suitable method may be used. Metal may also be recruited from intracellular or physiological environment.

Ligand Moieties

The ligand moieties of the present invention may be any molecular functionality which binds to a desired biochemical target with the desired kinetic properties; specifically, prefers $k_{off}$ values that are at least similar to the rate constant for the inactivation chemistry ($k_{cat}$). In certain embodiments, an affinity of a ligand for its target is between about $10^4 M^{-1}$ and about $5 \times 10^8 M^{-1}$. Such molecular functionalities with typically comprise an organic motif. In specific embodiments, the molecular functionality comprises one or more of a peptide backbone, a carbohydrate backbone, or a nucleic acid backbone. Exemplary molecules are secondary metabolites, antibodies, protein nucleic acids, aptamers, oligonucleotides, ribozymes, siRNAs, naturally occurring ligands for cellular receptors, etc. This list is not meant to be limiting.

With regard to antibodies, numerous publications discuss the use of phage display technology to produce and screen libraries of polypeptides for binding to a selected analyte with a desired affinity. See, e.g., Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities. See, e.g., Menger et al., Handb Exp Pharmacol. 173:359-73 (2006).

Aptamers include nucleic acid aptamers (i.e., single-stranded DNA molecules or single-stranded RNA molecules) and peptide aptamers. Aptamers bind target molecules in a highly specific, conformation-dependent manner. Aptamers have been shown to distinguish between targets based on very small structural differences such as the presence or absence of a methyl or hydroxyl group and certain aptamers can distinguish between D- and L-enantiomers. Numerous aptamers having affinity to a specific protein, DNA, amino acid and nucleotides have been described (e.g., K. Y. Wang, et al., Biochemistry 32:1899-1904 (1993); Pitner et al., U.S. Pat. No. 5,691,145; Gold, et al., Ann. Rev. Biochem. 64:763-797 (1995); Szostak et al., U.S. Pat. No. 5,631,146). Aptamers may have equilibrium dissociation constants ranging from micromolar to sub-nanomolar depending on the selection used.

Nucleic acid aptamers may be identified by an in vitro selection process known as "systematic evolution of ligands by exponential amplification" (SELEX). In the SELEX process very large combinatorial libraries of oligonucleotides, for example $10^{14}$ to $10^{15}$ individual sequences, often as large as 60-100 nucleotides long, are routinely screened by an iterative process of in vitro selection and amplification. Most targets are affinity enriched within 8-15 cycles and the process has been automated allowing for faster aptamer isolation. Peptide aptamers are typically identified by several different protein engineering techniques known in the art, including but not limited to, phage display, ribosome display, mRNA display, selectively infected phage I technology (SIP), and the like. Detailed descriptions of aptamers, including relevant protocols, can be found in, among other places, L. Gold, J. Biol. Chem., 270(23):13581-84 (1995); L. Gold et al., Ann. Rev. Biochem. 64:763-97 (1995); S. Jayashena, Clin. Chem., 45:1628-50 (1999); V. Sieber et al., Nat. Biotech. 16:955-60 (1998); L. Jermutus et al., Curr. Opin. i Biotech. 9:534-48 (1998); D. Wilson and J. Szostak, Ann. Rev. Biochem. 68:611 47 (1999); L. Jermutus et al., Eur. Biophys. J., 31:179-84 (2002); G. Connell et al., Biochem., 32:5497-5502 (1993); M. Famulok et al., Acc. Chem. Res. 33:591 99 (2000); W. James, Cum Opin. Pharmacol., 1:540-46 (2001); J. Cox. Et al., Nucl. Acid Res. 30(20):e18 (2002); S. Clark and V. Remcho, Electrophoresis i 23:1335-40, 2002; A. Tahiri-Alaoui et al., Nuc. Acid Res. 30(10):e45 (2002); A. Kopylov and V. Spiridonova, Molecular Biology 34:940-54 (2000); J. Blum et al., Proc. Natl. Acad. Sci., 97:2241-46 (2000); Phage Display: A Laboratory Manual, I C. Barbas, D. Burton, J. Scott, and G. Silverman, eds., Cold Spring Harbor Laboratory Press (2001); S. Jung et al., J. Mol. Biol. 294:163-80 (1999); N. Raffler et al., Chem. & Biol., 10:69-79 (2003); A. Pluckthun et al., Adv. Protein Chem. 55:367-403 (2000); Amstutz et al., Curr. Opin. Biotech., 12:400-05 (2001); J. Hanes and A. Pluckthun, Proc. Natl. Acad. Sci., 94:4937-42 (1997); Protein Protein Interactions, A Molecular Cloning Manual, E. Golemis, ea., Cold Spring Harbor Press (2001); C. Krebber et al., J. Mol. Biol. 268:607-18 (1997); S. Spada et al., Biol. Chem., 378:445-56 (1997); B. Wlotzka et al., Proc. Natl. Acad. Sci., 199:8898-8902 (2002); R. Roberts and J. Szostak, Proc. Natl. Acad. Sci., 94:12297-12302 (1997); P. Colas et al., Proc. Natl. Acad. Sci., 97:13720-25 (2000); and Y. Jiang et al., Anal. Chem., 75:2112-16 (2003).

Small molecule as used herein refers to an compound having an organic molecular scaffold with a molecular weight of 4000 daltons or less, or preferably 3000 daltons or less, 2000 daltons or less, 1000 daltons or less, 800 daltons or less, or 600 daltons or less. "Molecular scaffold" refers to a backbone structure to which one or more additional chemical moieties can be covalently attached, modified, or eliminated to form a plurality of molecules with common structural elements. The moieties can include, but are not limited to, a halogen atom, a hydroxyl group, a methyl group, a nitro group, a carboxyl group, or any other type of molecular group. Preferred characteristics of a scaffold can include the availability of sites to which one or more substituents may be positioned on the scaffold such that they are situated in binding pockets in a desired target molecule binding site; having chemically tractable structures that can be chemically modified, particularly by synthetic reactions, so that a combinatorial library can be easily constructed; having chemical positions where moieties can be attached that do not interfere with binding of the scaffold to a desired binding site, such that the scaffold or library members can be modified to achieve additional desirable characteristics, e.g., enabling the metallodrug to be actively transported into cells and/or to specific organs.

Small molecule combinatorial libraries may be purchased on the commercial market or prepared or obtained by any means including, but not limited to, combinatorial chemistry techniques, fermentation methods, plant and cellular extraction procedures and the like (see, e.g., Cwirla et al., (1990) Biochemistry, 87, 6378-6382; Houghten et al., (1991) Nature, 354, 84-86; Lam et al., (1991) Nature, 354, 82-84; Brenner et al., (1992) Proc. Natl. Acad. Sci. USA, 89, 5381-5383; R. A. Houghten, (1993) Trends Genet., 9, 235-239; E. R. Felder, (1994) Chimia, 48, 512-541; Gallop et al., (1994) J. Med. Chem., 37, 1233-1251; Gordon et al., (1994) J. Med. Chem., 37, 1385-1401; Carell et al., (1995) Chem. Biol., 3, 171-183; Madden et al., Perspectives in Drug Discovery and Design 2, 269-282; Lebl et al., (1995) Biopolymers, 37 177-198); small molecules assembled around a shared molecular structure; collections of chemicals that have been assembled by various commercial and noncommercial groups, natural products; extracts of marine organisms, fungi, bacteria, and plants.

Libraries of a variety of types of molecules are prepared in order to obtain library members having one or more preselected attributes that can be prepared by a variety of techniques, including but not limited to, those described by Houghton, (2000) Annu. Rev. Pharmacol. Toxicol. 40:273-82; Merritt, (1998) Comb. Chem. High Throughput Screen. 1 (2):57-72; Coe et al., (1998-99) Mol. Divers. 4(1):31-8; Sun, (1999) Comb. Chem. High Throughput Screen. 2(6):299-318; Gravert et al., (1997) Curr. Opin. Chem. Biol. 1(1):107-13; Dolle et al., (1999) J. Comb. Chem. 1(4):235-82; Freidinger R M., (1999) Current Opinion in Chemical Biology; and Kundu et al., Prog Drug Res, 53:89-156. Combinatorial synthesis of carbohydrates and libraries containing oligosaccharides have been described (Schweizer et al., (1999) Curr Opin Chem Biol 3(3):291-87). The synthesis of natural-product based libraries has been described (Wessjohann, (2000) Curr Opin Chem Biol 4(3):303-9).

Libraries of nucleic acids may be prepared by various techniques, including by way of non-limiting example the articles referred to herein for the isolation of aptamers. Nucleic acid libraries are known that can be coupled to parallel sampling and be deconvoluted without complex procedures such as automated mass spectrometry (Enjalbal C. Martinez J. Aubagnac J L, (2000) Mass Spectrometry Reviews. 19:139-61; Perrin D M., Combinatorial Chemistry & High Throughput Screening 3:243-69).

Peptidomimetics may be identified using combinatorial chemistry and solid phase synthesis (Kim H O. Kahn M., (2000) Combinatorial Chemistry & High Throughput Screening 3:167-83; al-Obeidi, (1998) Mol Biotechnol 9(3): 205-23).

Polypeptide libraries can be prepared according to venous techniques. In brief, phage display techniques can be used to produce polypeptide ligands (Gram H., (1999) Combinatorial Chemistry & High Throughput Screening. 2:19-28) that may be used as the basis for synthesis of peptidomimetics. Polypeptides, constrained peptides, proteins, protein domains, antibodies, single chain antibody fragments, antibody fragments, and antibody combining regions are displayed on filamentous phage for selection.

Exemplary peptide ligands for binding to various exemplary therapeutic targets (the sequences of which incorporate an N-terminal metal binding ATCUN motif (GGH, GGh, KGH, KKH)) include, but are not limited to, the following (C-terminal amidated unless otherwise noted):

```
Targeting HCV IRES RNA (SEQ ID NO: 10)
GGHGKYKETDLLILFKDDYFAKKNEERK (SEQ ID NO: 11)
GGHGKYKETDLLILFKDDYFAKKNEERKYGRKKRRQRRR (SEQ ID NO: 12)
GGHGKYKETDLLILFKDDYFAKKNEERKGGGYGRKKRRQRRR (SEQ ID NO: 13)
GGHKYKETDLLILFKDDYFAKKNEERKYGRKKRRQRRR (SEQ ID NO: 14)
GGHKYKETDLLILFKDDYFAKKNEERKGGGYGRKKRRQRRR (SEQ ID NO: 15)
GGHGKYKETDLLILFKDDYFAKKNEERKKDEL (SEQ ID NO: 16)
GGHGKYKETDLLILFKDDYFAKKNEERKGGGKDEL (SEQ ID NO: 17)
GGHGAALEAKICHQIEYYFGDF (SEQ ID NO: 18)
GGHAALEAKICHQIEYYFGDF GGHGYrFK GGHGYrFKGGGYGRKKRRQRRR GGHGYrFKGGGKDEL GGHYrFK GGhyrfk GGHYrFKGGGYGRKKRRQRRR GGHYrFKGGGKDEL (SEQ ID NO: 10)
GGHGKYKETDLLILFKDDYFAKKNEERK GGHYrFK-carboxylate KKHYrFK (SEQ ID NO: 19)
GGHKYKETDLLILFKDDYFAKKNEERK (SEQ ID NO: 20)
GGHKYKETDLLILFKDDYFAKKNEERKKDEL (SEQ ID NO: 21)
GGHKYKETDL
```

GGHKYKETDL-NH2 (SEQ ID NO: 22)

GGHYRFK-amide (SEQ ID NO: 23)

Targeting HCV Protease

GGHGDEMEECAS (SEQ ID NO: 24)

GGHGDEMEEC (carboxylate terminus) (SEQ ID NO: 25)

GGHGDeLI(Cha)CP(Cha)DL

GGHGDeLI(Cha)C (carboxylate terminus)

GGHGDEMEEC (SEQ ID NO: 26)

GGHGDEMEECASYSKDEL (SEQ ID NO: 27)

GGHGDLEVVT (SEQ ID NO: 28)

GGHGDLEVVTASYSKDEL (SEQ ID NO: 29)

GGHGDeL1(Cha)T

GGHGDeL1(Cha)TASYSKDEL

Targeting HIV protease

GGHGARVLAEAM (SEQ ID NO: 30)

GGHVLQNYPIVQ (SEQ ID NO: 31)

GGHGAEVFYVDGA (SEQ ID NO: 32)

Targeting HIV RRE RNA

GGHTRQARRNRRRRWRERQR (SEQ ID NO: 33)

KGHKTRQARRNRRRRWRERQR (SEQ ID NO: 34)

Targeting HIV TAR RNA

GGHGFTTKALGISYGRKKRRQRRRPPQGSQTHQVSLSKQ (SEQ ID NO: 35)

GGHFTTKALGISYGRKKRRQRRRPPQGSQTHQVSLSKQ (SEQ ID NO: 36)

GGHGRRRDRRLRQRARRR (SEQ ID NO: 37)

Targeting Sortase (antibacterial)

GGHLPETG (SEQ ID NO: 38)

GGHGLPETG (SEQ ID NO: 39)

GGHLPET (SEQ ID NO: 40)

GGHGLPET (SEQ ID NO: 41)

GGHLPET (carboxylate) (SEQ ID NO: 42)

Targeting Chaperone Protein (antibacterial)

GGHIKNYPARVKC (SEQ ID NO: 43)

GGHVSQFPARIKC (SEQ ID NO: 44)

GGHVSQFPARIK (SEQ ID NO: 45)

GGHLSLPPVKLHS (SEQ ID NO: 46)

GGHGQRKLFFNLRKTKQRLGWFNQC (SEQ ID NO: 47)

GGHGEYVLRNWRIVKVATTKAC (SEQ ID NO: 48)

Targeting Cardiovascular (sACE-1 and ECE-1)

KGHK (SEQ ID NO: 2)

GGHGGCHP (SEQ ID NO: 49)

GGHGGDHP (SEQ ID NO: 50)

GGHGIEP (SEQ ID NO: 51)

GGHGIKY (SEQ ID NO: 52)

GGHGIKW (SEQ ID NO: 53)

GGHGIKP (SEQ ID NO: 54)

GGHGGDF (SEQ ID NO: 55)

GGHGGDY (SEQ ID NO: 56)

Antimicrobial (unknown target, but active MIC)

GGHRAGLQFPVGRVHRLLRK (SEQ ID NO: 57)

GGHTRSSRAGLQFPVGRVHRLLRK (SEQ ID NO: 58)

GGHGIRRIIRKIIHIIKK (SEQ ID NO: 59)

GGHGVRRFPWWWPFLRR (SEQ ID NO: 60)

GGHGILAWKWAWWAWRR (SEQ ID NO: 61)

GGHGRLARIVVIRVAR (SEQ ID NO: 62)

GGHGGLFDIIKKIAESI (SEQ ID NO: 63)

Targeting 16S rRNA (antimicrobial)

GGHHPVHHYQ (SEQ ID NO: 64)

-continued

GGHGHPVHHYQ (SEQ ID NO: 65)

GGHGGHPVHHYQ (SEQ ID NO: 66)

GGHGLPLTPLP (SEQ ID NO: 67)

GGHGGLPLTPLP (SEQ ID NO: 68)

Targeting DNA Holliday junction (antimicrobial)

GGHGWRWYCR (SEQ ID NO: 69)

GGHGWRWYCR (SEQ ID NO: 69)

GGHGGWRWYCR (SEQ ID NO: 70)

Chemical Coupling

The metal binding and ligand moieties of the present invention may be coupled using chemical linkages well known in the art. Chemical cross-linkers are discussed in numerous books and catalogues. See, e.g., Wong, *Chemistry of Protein Conjugation and Cross-linking*, CRC Press, Boca Raton, Fla., 1991. These reagents often employ functional groups that couple to amino acid side chains of peptides. Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ε-amino groups, cysteine sulfhydryl groups, glutamic acid carboxyl groups, etc.), and selection of a particular functional moiety for inclusion in a sterol may be made empirically in order to best preserve a biological property of interest (e.g., binding affinity of an antibody, catalytic activity of an enzyme, etc.)

Coupling through Amine Groups:

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide.

Coupling through Sulfhydryl Groups:

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

Coupling Through Carboxyl Groups:

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

Nonselective Reactive Groups:

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

Coupling Through Arginines:

Glyoxals are useful compounds for targeting the guanidinyl portion of arginine residues. Glyoxals will target arginines at mildly alkaline pH. There is some cross-reactivity (the greatest at higher pH) with lysines.

Coupling Through Carbonyl Groups:

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones. For carbohydrates with reducing end(s), the carbonyl group(s) can be reactive towards a hydrazine moiety to form a hydrazone bond. S-HyNic is a heterobifunctional linker used to incorporate HyNic (6-hydrazinonicotinamide) moieties into molecules through a free amino group via an activated ester (i.e. NHS). The addition of a HyNic hydrazine linker permits formation of a conjugate in slightly acidic buffer (100 mM NaPO$_4$, pH6). For carbohydrates without a reducing end, CDAP specific activation may be used. Under mild conditions (pH 9.5 for activation and pH 7 for conjugation), 1-cyano-4-dimethylaminopyridinium tetrafluoroborate ("CDAP") converts hydroxyl groups to cyanyl esters which will then form carbamates in the presence of amine groups.

Polymeric substances may be optionally included in the linkage chemistry and/or in one of the functional moieties being linked. In one example, such polymeric substances are preferably poly(alkylene oxides). As used herein, the term "alkylene oxide" refers to the structure, —X—O—, where X is an alkylene moiety covalently linked to oxygen 0; thus poly(alkylene oxide) refers to the structure —(X—O—)$_m$—. It is preferred that the poly(alkylene oxide) polymer be a nonbranched homopolymer (i.e., a polymer of the structure —((CH$_2$)$_n$—O—)$_m$— in which n does not vary) such as poly(ethylene oxide) derived from ethylene glycol. Alternative polymers such as other polyalkylene oxide homopolymers (e.g., methylene oxide, propylene oxide, isopropylene oxide, and butylene oxide polymers) and co-polymers or block co-polymers of poly(alkylene oxides) may also be used. In those aspects of the invention where PEG-based polymers are used, it is preferred that they have average length ("m") of between 5 and 1000 monomeric units. Molar equivalent amounts of the other alkylene oxides may be determined readily by those of ordinary skill in the art to arrive at preferred average molecular weights for other homopolymers and copolymers.

Average molecular weights of the present invention are measured using the "number-average" method. In a mixture of polymer molecules with different molecular weights in which the number of molecules having a particular molecular weight, $M_i$ is given by $N_i$ the "number-average" probability of a given mass being present is $$P_i = \frac{N_i}{\sum_{j=0}^{\infty} N_j}$$

and the number-average molecular weight is given by the formula $$\overline{M_n} = \sum_{i=0}^{\infty} \left( \frac{N_i}{\sum_{j=0}^{\infty} N_j} \right) M_i = \frac{\sum_{i=0}^{\infty} N_i M_i}{\sum_{j=0}^{\infty} N_j}$$

The number average is the simple arithmetic mean, representing the total weight of the molecules present divided by the total number of molecules. The number-average molecular weight of a polymer may be measured by vapor pressure osmometry using methods and apparatuses well known to those of skill in the art.

Alternative polymeric substances which may be used in place of poly(alkylene oxides) include materials such as dextran, polyvinyl pyrrolidones, polysaccharides, starches, glycans, polyvinyl alcohols, polyacryl amides or other similar polymers. Those of ordinary skill in the art will realize that the foregoing is merely illustrative and not intended to restrict the type of non-antigenic polymeric substances suitable for use herein.

Biochemical Targets

The biochemical target of the present invention is a desired target for a ligand moiety. For example, in various embodiments, a ligand moiety is specific for or binds to a cellular component, which includes but is not limited to, epidermal growth factor receptor (EGFR, ErbB-1, HERD, ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family; platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family; TRK receptor family; ephrin (EPH) receptor family; AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor α receptors, TGFβ; Cytokine receptors, Class I (hematopoietin family) and Class II (interferon/IL-10 family) receptors, tumor necrosis factor (TNF) receptor superfamily (TNFRSF), death receptor family; cancer-testis (CT) antigens, lineage-specific antigens, differentiation antigens, alpha-actinin-4, ARTCl, breakpoint cluster region-Abelson (Bcr-abl) fusion products, B-RAF, caspase-5 (CASP-5), caspase-8 (CASP-8), β-catenin (CTNNB1), cell division cycle 27 (CDC27), cyclin-dependent kinase 4 (CDK4), CDKN2A, COA-I, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: β-D-galactose 2-α-L-fucosyltransferase (LDLR/FUT) fusion protein, HLA-Al 1, heat shock protein 70-2 mutated (HSP70-2M), KlAA0205, MART2, melanoma ubiquitous mutated 1, 2, 3 (MUM-I, 2, 3), prostatic acid phosphatase (PAP), neo-PAP, Myosin class I, NFYC, OGT, OS-9, pml-RARα fusion protein, PRDX5, PTPRK, K-ras (KRAS2), N-ras (NRAS), HRAS, RBAF600, SIRT2, SNRPD1, SYT-SSX1 or -SSX2 fusion protein, Triosephosphate Isomerase, BAGE, BAGK-1, BAGE-2, 3, 4, 5, GAGE-1, 2, 3, 4, 5, 6, 7, 8, GnT-V (aberrant N-acetyl glucosaminyl transferase V, MGAT5), HERV-K-MEL, KK-LC, KM-HN-I, LAGE, LAGE-I, CTL-recognized antigen on melanoma (CAMEL), MAGE-A1 (MAGE-I), MAGE-A2, MAGE-A3, MAGE-A4, MAGE-A5, MAGE-A6, MAGE-A8, MAGE-A9, MAGE-A10, MAGE-A11, MAGE-A12, MAGE-3, MAGE-B1, MAGE-B2, MAGE-B5, MAGE-B6, MAGE-C1, MAGE-C2, mucin 1 (MUC1), MART-1/Melan-A (MLANA), gp100, gp100/Pmel17 (SILV), tyrosinase (TYR), TRP-I, HAGE, NA-88, NY-ESO-I, NY-ESO-I/LAGE-2, SAGE, Sp17, SSX-1, 2, 3, 4, TRP2-INT2, carcinoembryonic antigen (CEA), Kallikrein 4, mammaglobin-A, OA1, prostate specific antigen (PSA), TRP-1/gp75, TRP-2, adipophilin, interferon inducible protein absent in melanoma 2 (AIM-2), BING-4, CPSF, cyclin D1, epithelial cell adhesion molecule (Ep-CAM), EphA3, fibroblast growth factor-5 (FGF-5), glycoprotein 250 (gp250), EGFR (ERBB1), HER-2/neu (ERBB2), interleukin 13 receptor α2 chain (IL13Ralpha2), IL-6 receptor, intestinal carboxyl esterase (iCE), alpha-feto protein (AFP), M-CSF, mdm-2, MUC1, p53 (TP53), PBF, PRAME, PSMA, RAGE-I, RNF43, RU2AS, SOXIO, STEAP1, survivin (BIRC5), human telomerase reverse transcriptase (hTERT), telomerase, Wilms' tumor gene (WT1), SYCP1, BRDT, SPANX, XAGE, ADAM2, PAGE-5, LIP1, CTAGE-I, CSAGE, MMA1, CAGE, BORIS, HOM-TES-85, AF15ql4, HCA661, LDHC, MORC, SGY-I, SPO1 1, TPX1, NY-SAR-35, FTHL17, NXF2, TDRD1, TEX15, FATE, TPTE, immunoglobulin idiotypes, Bence-Jones protein, estrogen receptors (ER), androgen receptors (AR), CD40, CD30, CD20, CD 19, CD33, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), β-human chorionic gonadotropin, β-2 microglobulin, squamous cell carcinoma antigen, neuron-specific enolase, heat shock protein gp96, GM2, sargramostim, CTLA-4, 707 alanine proline (707-AP), adenocarcinoma antigen recognized by T cells 4 (ART-4), carcinoembryogenic antigen peptide-1 (CAP-I), calcium-activated chloride channel-2 (CLCA2), cyclophilin B (Cyp-B), human signet ring tumor-2 (HST-2), Human papilloma virus (HPV) proteins (HPV-E6, HPV-E7, major or minor capsid antigens, others), Epstein-Barr virus (EBV) proteins (EBV latent membrane proteins—LMP1, LMP2; others), Hepatitis B or C virus proteins, and HIV proteins; or in each case, an RNA or DNA encoding any such protein or which is regulatory to the expression of such protein.

As noted herein, in various embodiments, a metallodrug of the invention comprises a ligand moiety which binds a component of an infectious agent, where such a compound is coupled to a biologically active agent, and wherein such a compound induces an immunostimulatory response (either directly/indirectly) in a subject. In general, such an infectious agent can be any pathogen including without any limitation bacteria, yeast, fungi, virus, eukaryotic parasites, etc. In various embodiments, compounds of the invention comprise a ligand moiety directed to a component present on a pathogen/infectious agent, which include but are not limited to Retroviridae (e.g. human immunodeficiency viruses, such as HIV-I (also referred to as HTLV-III, LAV or HTLV-III/LAV, or HIV-III); and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)), D-type retroviruses include Mason-Pfizer monkey virus (MPMV) and simian retrovirus type 1 (SRV-I), the complex retroviruses including the subgroups of lentiviruses, T-cell leukemia viruses and the foamy viruses, lentiviruses including HIV-I, HIV-2, SIV, Visna virus, feline immunodeficiency virus (FIV), and equine infectious anemia virus (EIAV), simian T-cell leukemia virus (STLV), and bovine leukemia virus (BLV), the foamy viruses including human foamy virus (HFV), simian foamy virus (SFV) and bovine foamy virus (BFV), Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (i.e. Hepatitis C); Norwalk and related viruses, and astroviruses), *Mycobacterium (Mycobacterium tuberculosis, M. bovis, M. avium-intracellulare, M. leprae), Pneumococcus, Streptococcus, Staphylococcus, Corynebacteria Listeria, Erysipelothrix, Bacillus* (e.g., *B. anthracis), Clostridium* (e.g., *C. tetani, C. perfringens),* Mixed Anaerobes, *Neisseria, Salmonella, Shigella, Hemophilus, Burkholderi, Escherichia* (e.g., *E. coli), Klebsiella, Enterobacter, Serratia, Pseudomonas, Bordatella, Francisella* (e.g., *F. tularensis), Yersinia, Vibrio* (e.g., *V. cholerae), Bartonella, Legionella, Spirochaetes (Treponema, Leptospira, Borrelia),* Fungi, *Actinomyces, Rickettsia, Mycoplasma, Chlamydia,* Protozoa (including *Entamoeba, Plasmodium, Leishmania, Trypanosoma, Toxoplasma, Pneumocystis, Babasia, Giardia, Cryptosporidium, Trichomonas),* Helminths (*Trichinella, Wucheraria, Onchocerca, Schistosoma,* Nematodes, Cestodes, *Trematodes).*

Each of the foregoing and subsequent lists is illustrative, and is not intended to be limiting.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy $21^{st}$ Edition (Mack Publishing Co., Easton, Pa.) and Nielloud and Marti-Mestres, Pharmaceutical Emulsions and Suspensions: $2^{nd}$ Edition (Marcel Dekker, Inc, New York).

For the purposes of this disclosure, the pharmaceutical compositions may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide. slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the compounds of formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., PA; Chabner and Longo (eds.) (2001) Cancer Chemotherapy and Biotherapy, Lippincott, Williams & Wilkins, Phila., PA).

EXAMPLES

The following examples serve to illustrate the present invention. These examples are in no way intended to limit the scope of the invention.

Example 1

Relationship Between Kinetic/Thermodynamic Data in Controlling Catalytic MetalloDrug Efficiency A range of metallopeptide derivatives have been examined with affinities varying from 10 nM (Gly-Gly-His-Asp-D-Glu-Leu-11e-Cha-Cys-Pro-Cha-Asp-Leu) to 48 uM (Gly-Gly-His-Asp-Glu-Met-Glu-Glu-Cys (SEQ ID NO: 71)). A comparison of relative binding affinity versus catalytic efficiency for HCV protease inactivation reveals an inverse correlation between these parameters. This stems from the relationship between affinity and the on/off rate constants for binding ($K_{assoc}=k_{on}/k_{off}$), where higher affinity binding is promoted by larger $k_{on}$ and/or smaller $k_{off}$ values. By contrast, efficient catalytic turnover requires $k_{off}$ values that are preferably no smaller than the rate constant for the inactivation chemistry ($k_{cat}$), to ensure the availability of metallodrug catalyst for new target molecules, and will be best promoted by relatively high values for both $k_{on}$ and $k_{off}$, which will result in weaker $K_{assoc}$ values. Those metallodrugs with weaker binding affinity are, in fact, observed to promote more efficient inactivation of the HCV protease (FIGS. 1 and 2), consistent with the more rapid release of metallodrug catalyst from the HCV protease following oxidative modification of amino acids. FIG. 1 illustrates results for a peptide with 500 nm affinity, but with low catalytic efficiency 0.083 h$^{-1}$, while a second peptide with lower affinity 48 µM (FIG. 2) shows higher catalytic efficiency 1.6 h$^{-1}$.

A traditional drug model typically requires binding affinities on the order of low nM to pM to achieve saturation binding of the drug target without the need for high drug concentrations that could also exacerbate secondary non-selective binding to other biological components with increasing side-effects and/or toxicity. For example, the HCV protease inhibitor BILN 2061 developed by Boehringer Ingelheim Pharma (BILN 2061) demonstrated an inhibition constant 0.3 nM. Design efforts toward this molecule were based on a weak hexapeptide inhibitor Asp-Asp-Ile-Val-Pro-Cys (SEQ ID NO: 72) ($K_I$ of 79 µM). In Boehringer's development work a lower affinity peptide formed the basis for rational redesign to increase $K_I$ from 79 µM to 0.3 nM and thereby provide a more potent traditional inhibitor. Clearly the synthesis of a peptide molecule is considerably simpler than the complex multi-step synthesis required to turn a peptide into a high affinity binding ligand. Moreover, while several HCV protease candidates display equally "poor" binding affinities in the higher pM range, they actually display the highest levels of catalytic inactivation of target HCV protease (FIGS. 1 and 2).

Example 2

Buforin II Metallodrugs

Buforin II is a 21-amino acid antimicrobial peptide having antimicrobial activity against a broad spectrum of microbial organisms, including Gram-positive and Gram-negative bacteria, as well as fungi. The buforin peptide adopts an amphipathic helical structure in a hydrophobic environment, and has been shown to penetrate the membrane of target cells and bind to nucleic acids within the cells at micromolar concentrations.

A copper ATCUN derivative of buforin II (CuGGH-TRSS-RAGLQFPVG RVHRLLRK (SEQ ID NO: 73)) was synthesized and the activity of the derivative was compared to that of the native buforin II sequence by assessing the sensitivity of various bacterial species as measured by establishing the Minimum Inhibitory Concentration (MIC).

Relative MIC determinations were established by standard broth dilution methods using nutrient broth and a cell density corresponding to $10^5$ colony forming units in a 200 µL volume. MIC values were determined as the lowest concentration of drug at which there was no visible growth after 12 h incubation. Metallodrug derivitization enhanced MIC by at least 100-fold relative to the antimicrobial buforin II peptide against the following bacterial strains—E. coli (ATCC 25922); P. aeruginosa (ATCC 27583); K. pneumoniae (ATCC 00603); S. aureus (MRSA ATCC 43300).

Example 3

Lisinopril Metallodrugs Targeting Angiotensin-Converting Enzyme (ACE)

Lisinopril was purchased from Cayman Chemical Company and stored at −20° C. in powder form, and ESI-TOF-MS analysis confirmed the expected mass of 404 amu. Recombinant human somatic ACE (sACE-1: Leu30-Leu1261, with C-terminal His tag, >95% purity by SDS-PAGE under reducing conditions), originally isolated from an NS0-derived murine myeloma cell line, was purchased from R&D Systems as a stock solution containing 12.5 mM Tris, 75 mM NaCl, 0.5 M $ZnCl_2$, and 40% (v/v) glycerol, pH 7.5 with [sACE-1]= 0.434 mg/mL, and divided into single use aliquots prior to storing at −20° C. Fluorogenic substrate Mca-RPPGFSAFK (Dnp)-OH (SEQ ID NO: 74) was purchased from R&D Systems, dissolved in DMSO, divided into single use aliquots, and stored at −20° C. The bifunctional compound NHS-DOTA was purchased from Macrocyclics and stored at −20° C. in powder form. N-hydroxysuccinimide (NHS) was purchased from GenScript, and 1-ethyl-3-[3-dimethyl aminopropyl]carbodiimide hydrochloride (EDC) was purchased from Pierce and stored at −20° C. Ethylenediamine-tetraacetic acid (EDTA) was purchased from Aldrich. Nitrilotriacetic acid (NTA) was purchased from Sigma. The tripeptides GGH-OH (GGH) and Z-GGH-OH (Z-GGH; Z=carboxybenzyl) were obtained from Bachem, and 1,4,7,10-tetraazacyclododecane-1,4,7,10-tetraacetic acid (DOTA) was purchased from Macrocyclics. The Fe(II) sulfate heptahydrate, Co(II) chloride hexahydrate, Ni(II) acetate tetrahydrate, Cu(II) chloride dihydrate, and Zn(II) chloride salts were purchased from ACROS, J. T. Baker, Aldrich, J. T. Baker, and MCB Reagents, respectively. Sodium chloride, sodium hydroxide, and ammonium persulfate were purchased from Fisher. HEPES was purchased from Sigma. Acetonitrile, SDS, and $Na_2HPO_4$ were purchased from Sigma-Aldrich, $NaHCO_3$ was purchased from Mallinckrodt, 40% acrylamide/Bis solution (19:1) was purchased from Bio-Rad, and TFA was purchased from ACROS. The silver stain kit was purchased from Pierce. The C18 preparatory and analytical columns used for RP-HPLC were purchased from Vydac, and the PolyWAX LP column used for anion exchange HPLC was purchased from PolyLC. $D_2O$ (99.96%) for $^1$H-NMR was purchased from Cambridge Isotopes Laboratory.

EDTA-lisinopril was prepared by making a solution containing 500 mM EDTA, 500 mM NHS, 500 mM EDC in DMSO and reacting for 20 min at ambient temperature. After 20 min, 48 µL of this reaction mixture was mixed with 552 µL of a solution that contained 22 mM lisinopril in 100 mM $NaHCO_3$, pH 8.0. The reaction proceeded overnight at RT in the dark, followed directly by anion exchange HPLC purification. Anion exchange elution conditions used a gradient method, running from 0 to 100% B from 0 to 50 min, and 100% B from 50 to 55 min, where mobile phase A=10 mM $Na_2HPO_4$, pH 5.7; and B=1 M NaCl, 10 mM $Na_2HPO_4$, pH 5.7. The anion exchange HPLC fraction for product EDTA-lisinopril was collected and further separated by RP-HPLC. RP-HPLC elution conditions used a gradient method, running from 15 to 65% B from 0 to 45 min, 65 to 95% B from 45 to 50 min, and 95% B from 50 to 55 min where mobile phase A=$H_2O$, 0.1% TFA; B=acetonitrile, 0.1% TFA. The RP-HPLC fraction for product EDTA-lisinopril was collected, lyophilized, resuspended in water, and ESI-TOF MS analysis provided the expected mass of 678 amu (negative mode), as well as the +$Na^+$-1$H^+$ adduct at 700 amu, with no evidence of uncoupled lisinopril reactant (404 amu). EDTA-lisinopril concentration was quantified via UV/Vis (270 nm) titration with a solution of known concentration of copper(II) chloride.

NTA-lisinopril was prepared by making a solution containing 500 mM NTA, 500 mM NHS, and 500 mM EDC in DMSO and reacting for 20 min, after which time 48 µL of the reaction volume was mixed with 552 µL of a solution that contained 22 mM lisinopril in 100 mM $NaHCO_3$, pH 8.0. The reaction proceeded overnight at RT in the dark, followed by consecutive HPLC purification (first anion exchange, then RP-HPLC) using the same elution conditions as used for EDTA-lisinopril. The RP-HPLC fraction for product NTA-lisinopril was collected, lyophilized, resuspended in water, and ESI-LCQ MS analysis provided the expected mass of 578 amu (negative mode), with no evidence of uncoupled lisinopril reactant. NTA-lisinopril concentration was quantified via UV/Vis (250 nm) titration with a solution of known concentration of iron(II) sulfate.

DOTA-lisinopril was prepared by making a solution containing 40 mM NHS-DOTA (10× stock made in DMSO) and 20 mM lisinopril in 100 mM $NaHCO_3$, pH 8.0. The reaction proceeded overnight at RT in the dark, followed by consecutive HPLC purification (first anion exchange, then RP-HPLC) using the same elution conditions as used for EDTA-lisinopril. The RP-HPLC fraction for product DOTA-lisinopril was collected, lyophilized, resuspended in water, and ESI-TOF MS analysis provided the expected mass of 791 amu (negative mode), with no evidence of uncoupled lisinopril reactant. DOTA-lisinopril concentration was quantified via UV/Vis (240 nm) titration with a solution of known concentration of nickel(II)acetate.

GGH-lisinopril was prepared by making a solution containing 200 mM Z-GGH (Z=carboxybenzyl), 200 mM NHS, 200 mM EDC in DMSO and reacting for 20 min, after which time 54 µL of this reaction volume was mixed with 30 µL of 200 mM lisinopril in DMSO. The reaction proceeded overnight at RT in the dark, followed by consecutive HPLC purification (first anion exchange, then RP-HPLC) using the same elution conditions as used for EDTA-lisinopril. The RP-HPLC fraction for product Z-GGH-lisinopril was collected and lyophilized. ESI-TOF MS analysis provided the expected mass for Z-GGH-lisinopril of 789 amu with no evidence of uncoupled lisinopril reactant. The lyophilized Z-GGH-lisinopril was deprotected by dissolving in 1 mL TFA, and 5 mg 20% $Pd(OH)_2$ on charcoal was added and stirred to form a slurry. The mixture was Ar-purged and the anaerobic solution was reacted under a positive pressure of $H_2$ for ~6 hrs. The mixture was dried under vacuum, redissolved in water, and centrifuged to remove solid catalyst, and the resulting deprotected GGH-lisinopril was purified by RP-HPLC using the same RP-HPLC conditions as used for EDTA-lisinopril. The RP-HPLC fraction for product GGH-lisinopril was collected, lyophilized, resuspended in water, and ESI-TOF MS analysis provided the expected mass of 655 amu (negative mode), as well as the $+Na^+-1H^+$ adduct at 677 amu, with no evidence of uncoupled lisinopril reactant. The concentration of product GGH-lisinopril was quantified via UV/Vis (245 nm) titration with a solution of known concentration of nickel(II)acetate.

A summary of the metal chelate complexes and their attachment to the lysine sidechain of lisinopril is provided in FIG. 3 ($M=Fe^{3+}$, $Co^{2+}$, $Ni^{2+}$, $Cu^{2+}$; R=N(H)-lisinopril). The identities and isomeric purity of the synthesized chelate-lisinopril compounds were validated by $^1$H-NMR analysis, analytical RP-HPLC, and ESI-MS. Divalent iron, cobalt, nickel, and copper complexes of DOTA-lisinopril, EDTA-lisinopril, NTA-lisinopril, and GGH-lisinopril were prepared by mixing the respective metal salts with the chelate-lisinopril species in a buffer containing 20 mM HEPES, 100 mM NaCl, pH 7.4 and mixing at RT for 30 min prior to each measurement. M-chelate complex formation was verified by metal ion titration monitored by UV/vis. Metal:chelate ratios of 1:1 and 1:1.1 (to ensure that essentially all metal was chelated) were used for concentration-dependent and time-dependent inactivation experiments, respectively. The $Fe^{2+}$ complex with GGH-lisinopril was not used in later experiments due to weak complex formation.

Determination of $IC_{50}$ Values. sACE-1 (1 nM) and variable concentrations of each M-chelate-lisinopril complex (prepared in the absence of $Zn^{2+}$) were incubated for 20 min at 37° C. in a buffer containing 50 mM HEPES, 300 mM NaCl, 10 µM $ZnCl_2$, 0.05% Brij35, pH 7.4. After 20 min, 68.6 µL of each preincubated mixture of sACE-1 and inhibitor were mixed with 1.4 µL of 0.5 mM fluorogenic substrate in a fluorescence cuvette, and substrate cleavage by sACE-1 was immediately monitored by real-time fluorimetry at 37° C., with excitation at 320 nm and emission at 405 nm. Initial rates of fluorescence increase were determined for each concentration of M-chelate-lisinopril, and these initial rates were expressed as a percentage (% maximal activity) of the average of several initial rates of uninhibited substrate cleavage by sACE-1 in the absence of M-chelate-lisinopril complexes. Plots of % maximal activity vs. M-chelate-lisinopril concentration were fit to equation (1), where A, [I], n, and [$IC_{50}$] are the % maximal activity, inhibitor concentration, fitted cooperativity, and fitted $IC_{50}$ respectively. $IC_{50}$ values were determined for each M-chelate-lisinopril, chelate-lisinopril, M-chelate, and chelator species.

$$A=(100\%)/[1+([I]/[IC_{50}])^n] \quad (1)$$

Time-Dependent Inactivation of sACE-1. sACE-1 and each M-chelate-lisinopril complex (prepared in the absence of $Zn^{2+}$) were preincubated for 20 min at 37° C. in a buffer containing 50 mM HEPES, 300 mM NaCl, 10 µM $ZnCl_2$, 0.05% Brij35, pH 7.4, and after 20 min, coreactants ascorbate and/or $H_2O_2$ (or no coreactants) were added to initiate each reaction. Reaction concentrations were 1 nM sACE-1, a concentration of M-chelate-lisinopril that gave approximately 80% activity (calculated by use of equation (1), where A=80%; concentrations listed in the table in paragraph [00132]), and 1 mM ascorbate and/or $H_2O_2$ (or no coreactants). Each time-dependent ACE-inactivation reaction proceeded at 37° C. for a period of 2 h, and at each specific intervening time point, a 68.6 µL aliquot of the reaction mixture containing sACE-1 was mixed with 1.4 µL of 0.5 mM fluorogenic substrate in a fluorescence cuvette. Substrate cleavage by sACE-1 was immediately monitored by real-time fluorimetry at 37° C., with excitation at 320 nm and emission at 405 nm. Initial rates were determined for each time point for the time-dependent inactivation of sACE-1, and these initial rates were expressed as a percentage (% maximal activity) of the average of several initial rates for uninhibited substrate cleavage by sACE-1, determined in the absence of both M-chelate-lisinopril complexes and coreactants. Plots of % maximal activity vs. time were fit to a first-order exponential decay model, and initial rates of inactivation of sACE-1 by M-chelate-lisinopril complexes were determined. Second-order rate constants for inactivation of sACE-1 were obtained using equation (2), where $k_2$ is the second-order rate constant ($M^{-1}$ $min^{-1}$), R is the initial rate of enzyme inactivation (M/min) after subtraction of the corresponding background rate in the absence of M-chelate-lisinopril complex, but with the same coreactants, [I] is the concentration of M-chelate-lisinopril complex used (M), and [E] is the concentration of sACE-1 used ($1\times10^{-9}$ M). Control experiments with M-chelate complexes lacking attached lisinopril were performed in the same manner and conditions used for the respective M-chelate-lisinopril complexes.

$$k_2=R/[I]/[E] \quad (2)$$

Second order rate constants for both inactivation and cleavage of full length sACE-1 by several M-chelate-lisinopril complexes and control experiment second order rate constants for the corresponding M-chelates lacking lisinopril, and $IC_{50}$'s for sACE-1 inhibition by metal-chelate-lisinopril complexes are provided in the following table.

| | Second order rate constant for inactivation (and cleavage) of full length sACE-1 ($M^{-1}min^{-1}$)[b] | | | | |
|---|---|---|---|---|---|
| Complex[a] | M-chelate-lisinopril conjugate | M-chelate without lisinopril | IC50's (nM) | Affinities based on IC50's ($M^{-1}$) | Conditions[c] |
| Cu-GGH-lisin | 152,000 ± 7,000 {70,000 ± 20,000} | 10,000 ± 5,000 {<3,000} | 1,470 ± 20 | $0.68 \times 10^6$ | Ascorbate + $H_2O_2$ |
| Fe-EDTA-lisin | 110,000 ± 30,000 {<100,000} | 10,000 ± 50,000 {<100,000} | 88 ± 5 | $1.14 \times 10^7$ | Ascorbate |

-continued

| Complex[a] | Second order rate constant for inactivation (and cleavage) of full length sACE-1 ($M^{-1}min^{-1}$)[b] | | IC50's (nM) | Affinities based on IC50's ($M^{-1}$) | Conditions[c] |
|---|---|---|---|---|---|
| | M-chelate-lisinopril conjugate | M-chelate without lisinopril | | | |
| Cu-GGH-lisin | 102,000 ± 6,000 {<6,000} | <1,000 {—[d]} | 1,470 ± 20 | $0.68 \times 10^6$ | Ascorbate |
| Co-GGH-lisin | 70,000 ± 40,000 {<70,000} | <20,000 {—[d]} | 90 ± 10 | $1.11 \times 10^7$ | Ascorbate + $H_2O_2$ |
| Co-EDTA-lisin | 40,000 ± 10,000 {10,000 ± 7,000} | <4,000 {—[d]} | 1,200 ± 40 | $0.83 \times 10^6$ | $H_2O_2$ |
| Co-EDTA-lisin | 30,000 ± 10,000 {<3,000} | <3,000 {—[d]} | 1,200 ± 40 | $0.83 \times 10^6$ | Ascorbate + $H_2O_2$ |
| Ni-GGH-lisin | 30,000 ± 20,000 {<60,000} | <5,000 {—[d]} | 150 ± 30 | $6.67 \times 10^6$ | Ascorbate |
| Cu-GGH-lisin | 28,000 ± 9,000 {15,000 ± 6,000} | <2,000 {—[d]} | 1,470 ± 20 | $0.68 \times 10^6$ | $H_2O_2$ |
| Fe-DOTA-lisin | 22,000 ± 5,000 {<2,000} | <600 {—[d]} | 3,800 ± 400 | $0.26 \times 10^6$ | $H_2O_2$ |
| Fe-DOTA-lisin | 8,000 ± 1,000 {3,000 ± 1,000} | <400 {—[d]} | 3,800 ± 400 | $0.26 \times 10^6$ | Ascorbate + $H_2O_2$ |
| Ni-DOTA-lisin | 7,000 ± 1,000 {<600} | <700 {—[d]} | 4,500 ± 200 | $2.2 \times 10^5$ | Ascorbate + $H_2O_2$ |
| Cu-DOTA-lisin | 6,200 ± 900 {<1,000} | <500 {—[d]} | 4,400 ± 400 | $2.3 \times 10^5$ | Ascorbate + $H_2O_2$ |
| Cu-EDTA-lisin | 5,000 ± 4,000 {<9,000} | <3,000 {—[d]} | 960 ± 60 | $1.04 \times 10^6$ | $H_2O_2$ |
| Co-DOTA-lisin | 5,000 ± 1,000 {2,000 ± 2,000} | <700 {—[d]} | 4,100 ± 200 | $2.4 \times 10^5$ | Ascorbate + $H_2O_2$ |
| Cu-EDTA-lisin | 3,000 ± 2,000 {2,000 ± 9,000} | 2,000 ± 3,000 {—[d]} | 960 ± 60 | $0.1 \times 10^7$ | Ascorbate |
| Cu-DOTA-lisin | 1,000 ± 400 {<2,000} | <1,000 {—[d]} | 4,400 ± 400 | $2.3 \times 10^5$ | Ascorbate |
| Lisinopril | 1.9 ± 0.3 | — | 1.9 ± 0.3 | $5.2 \times 10^8$ | — |
| [Cu-DOTA]$^{2-}$ | na[e] | na[e] | 30,000 ± 2,000 | $3.3 \times 10^4$ | |
| [Cu-EDTA]$^{2-}$ | na[e] | na[e] | 26,000 ± 5,000 | $3.8 \times 10^4$ | |
| [Cu-NTA]$^{1-}$ | na[e] | na[e] | 36,000 ± 4,000 | $2.8 \times 10^4$ | |
| [Cu-GGH]$^{1-}$ | na[e] | na[e] | 17,000 ± 2,000 | $5.9 \times 10^4$ | |

Figure 4:
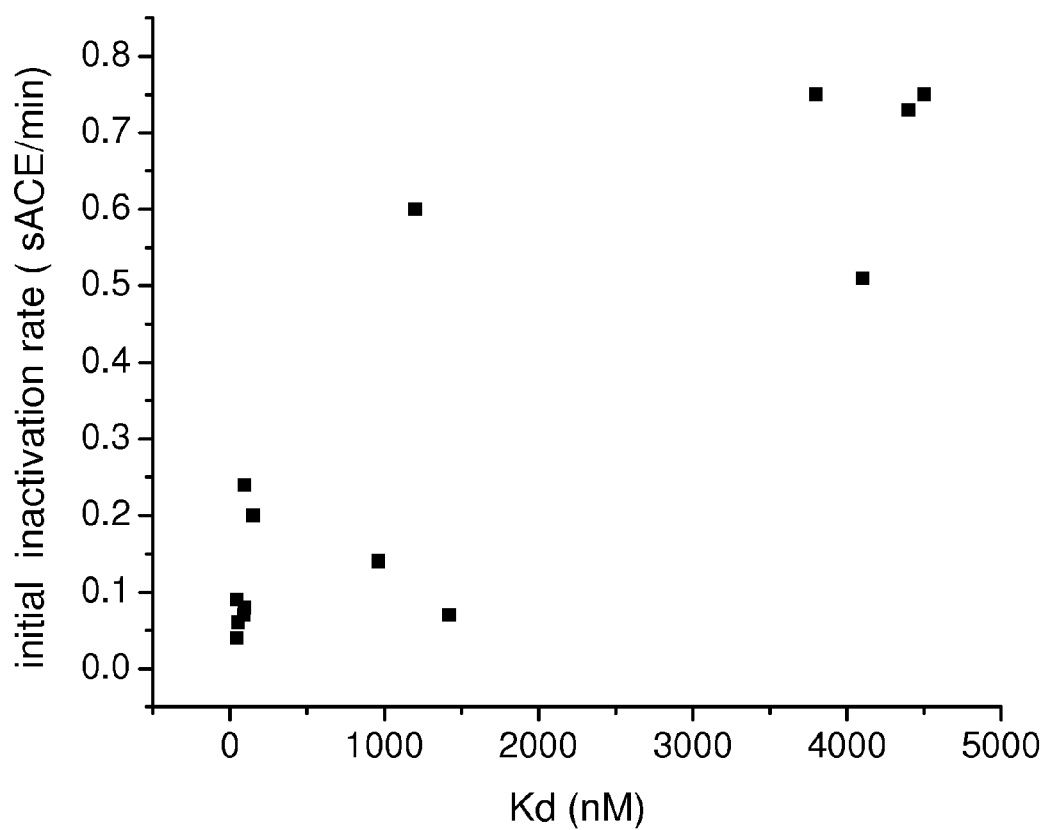
FIG. 4: A graphic depiction of variations in activity plotted against affinity for exemplary lisinopril metallodrugs, showing an increase in inactivation activity with weaker binding of the metallodrug.

[a]lisin = lisinopril.
[b]Second order rate constants for inactivation of sACE-1 (measured by substrate cleavage) and for cleavage of full length sACE-1 (monitored by SDS-PAGE) are listed for comparison (shown in brackets).
[c]All experiments throughout this study were performed at pH 7.4, 37° C.
[d]Not determined.
[e]not applicable Targeting sACE-1. With the exception of the Cu-GGH-lisinopril conjugate, which carries a metal chelate with a distinct reduction potential, all other complexes show a general trend of decreasing activity with increasing affinity (FIG. 4). Scatter reflects the prevalence of other factors (steric, electronic, positioning of metal associated reactive oxygen species to scissile bonds) that also play a role in dictating activity, emphasizing the point that higher affinity binding does not in itself promote efficient reactivity Example 4

Regulator of Virion Expression (REV) Metallodrugs Targeting HIV RRE RNA

Custom RNAs were purchased from Dharmacon and included AP-RRE RNA, with sequence 5'-GGUCUGGGCGCAGCGCAAGCUGACGG(2-AP)ACAGGCC-3' (SEQ ID NO: 75), and FI-RRE RNA, with sequence 5'-Fluorescein-UUGGUCUGGGCGCAGCGCAAGCUGACGGUACAGG-CC-3' (SEQ ID NO: 76). The N-terminal acetylated and C-terminal amidated peptide (K-Rev) with sequence Ac-KTRQARRNRRRRWRERQR-$NH_2$ (SEQ ID NO: 77) used for coupling reactions was purchased from Neo Peptide. The peptides GGH-Rev with sequence GGHTRQARRNRRRRWRERQR-$NH_2$ (SEQ ID NO: 78) and KGHK-Rev (SEQ ID NO: 2) with sequence KGHKTRQARRNRRRRWRERQR-$NH_2$ (SEQ ID NO: 79) were purchased from Genemed Synthesis Inc. RNA and peptide species were immediately aliquoted into single-use containers and stored at −20° C. to minimize freeze-thaw cycles. The bifunctional compounds NHS-DOTA and p-SCN-Bn-DTPA were purchased from Macrocyclics and stored at −20° C. N-hydroxysuccinimide (NHS) was purchased from GenScript, and 1-ethyl-3-[3-dimethyl aminopropyl]carbodiimide hydrochloride (EDC) was purchased from Pierce and stored at −20°

C. Ethylenediaminetetraacetic acid (EDTA) was purchased from Aldrich. Nitrilotriacetic acid (NTA) and diethylenetriaminepentaacetic acid (DTPA) were purchased from Sigma. The tripeptide GGH-OH (GGH) and tetrapeptide KGHK-NH$_2$ (SEQ ID NO: 80) (KGHK (SEQ ID NO: 2)) were obtained from Bachem, and 1,4,7,10-tetraazacyclododecane-1,4,7,10-tetraacetic acid (DOTA) was purchased from Macrocyclics. The Fe(II) sulfate heptahydrate, Co(II) chloride hexahydrate, Ni(II) tetrahydrate, and Cu(II) chloride dihydrate salts were purchased from ACROS, J. T. Baker, Aldrich, and J. T. Baker, respectively. Sodium chloride and sodium hydroxide were purchased from Fisher, and HEPES was purchased from Sigma.

DOTA-Rev was prepared by making a solution containing 3.8 mM NHS-DOTA (10× stock made in DMSO) and 757 µM K-Rev in a buffer containing 100 mM NaHCO$_3$, pH 8.0. The reaction proceeded for 2 h at RT in the dark, followed by RP-HPLC purification. Elution conditions were: 15-35% B, 0-50 min; 35-100% B, 50-55 min; 100% B, 55-60 min where mobile phase A=H$_2$O, 0.1% TFA; B=acetonitrile, 0.1% TFA. The HPLC fraction for product DOTA-Rev was collected, lyophilized, resuspended in water, and MALDI-TOF analysis provided the expected mass 2992.3 amu, with no evidence of uncoupled K-Rev reactant. DOTA-Rev concentration was quantified via UV/Vis (240 nm) titration with a solution of known concentration of nickel(II)acetate.

EDTA-Rev and NTA-Rev were made separately by first preparing a solution of 38 mM EDTA (or NTA), 38 mM NHS, 15.6 mM EDC in a buffer containing 20 mM HEPES, 100 mM NaCl, pH 5.7 and allowed to react for 1 min. After 1 min, K-Rev was added to a final concentration of 757 µM. The reaction proceeded for 2-4 h at RT in the dark, followed by RP-HPLC purification. Elution conditions were: 15-20% B, 0-50 min; 20-100% B, 50-55 min; 100% B, 55-60 min where mobile phase A=H$_2$O, 0.1% TFA; B=acetonitrile, 0.1% TFA. Due to poor separation and <100% coupling, the collected HPLC fraction containing a mixture of the coupled and unreacted K-Rev was lyophilized, resuspended in water and recycled through the above procedure with additional EDTA (or NTA) to increase yield, and RP-HPLC purification was repeated. The lyophilized HPLC fraction was resuspended in water, and the EDTA-Rev and NTA-Rev concentrations were determined by UV/Vis titrations with solutions of known concentrations of CuCl$_2$ (at 270 nm) and FeSO$_4$ (at 250 nm), respectively. The purity of the coupled K-Rev product (also a measure of the extent of coupling) was determined by comparison of the concentration of coupled EDTA (or NTA) determined by metal ion titration, and the concentration of the internal Trp residue of EDTA-Rev/K-Rev (or NTA-Rev/K-Rev) independently determined by absorbance at 280 nm. Coupling efficiency was found to be 83% (EDTA-Rev) and 137% (NTA-Rev)—it remains unclear why the apparent extent is >100%, and it may be a data fitting artifact. MALDI analysis provided the expected masses of 2880.7 and 2779.7 amu for EDTA-Rev and NTA-Rev, respectively, as well as the remaining uncoupled K-Rev (2606.9 amu) reactant.

DTPA-Rev was prepared from a solution containing 3.8 mM p-SCN-Bn-DTPA (10× stock made in DMSO) and 757 µM K-Rev in a buffer containing 100 mM NaHCO$_3$, pH 9.0. The reaction proceeded for 2 h at RT in the dark, followed by RP-HPLC purification using the same elution conditions as used for DOTA-Rev. The HPLC fraction for DTPA-Rev was collected, lyophilized, resuspended in water, and MALDI-TOF analysis provided the expected mass of 3146.4 amu for DTPA-Rev as well as a much smaller amount of residual K-Rev at 2606.9 amu. Both DTPA-Rev and K-Rev products were easily separable via HPLC, and so the observed K-Rev at 2606.9 amu may be artifactual from the MALDI analysis. The DTPA-Rev concentration was quantified by UV/Vis (290 nm) titration with a solution of known concentration of CuCl$_2$.

Figure 5:
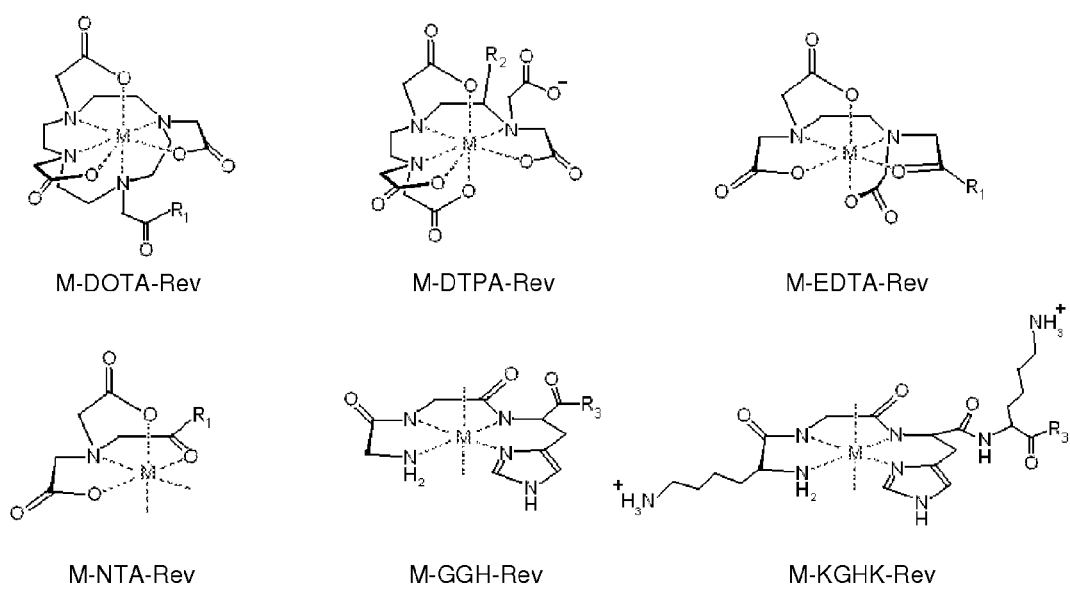
FIG. 5: Exemplary REV peptide metallodrugs of the present invention that target HIV RRE RNA.

Divalent iron, cobalt, nickel, and copper complexes of DOTA-Rev, DTPA-Rev, EDTA-Rev, NTA-Rev, GGH-Rev, and KGHK-Rev (SEQ ID NO: 2) were prepared by mixing the respective metal salts with the chelate-Rev species in a 1:1.2 ratio (to ensure essentially all metal was chelated) and mixing at RT for 30 min prior to each measurement. Metal-chelate complex formation was verified by UV/Vis titration. Fe$^{2+}$ complexes with chelators GGH-Rev and KGHK-Rev (SEQ ID NO: 2) were not used in later experiments due to insufficient complex formation. A summary of the metal-chelate complexes and their modes of attachment to the Rev peptide is provided in FIG. 5 (M=Fe$^{2+}$, Co$^{2+}$, Ni$^{2+}$, Cu$^{2+}$; R$_1$=N(H)-K-Rev; R$_2$=p-Bn-N(H)C(S)-K-Rev; R$_3$=N(H)-Rev).

Determination of Dissociation Constants. Dissociation constants (K$_D$) were determined by fluorimetry on a Varian Cary Eclipse fluorescence spectrophotometer with excitation at 310 nm (SW=10 nm) and emission at 371 nm (SW=10 nm). A 660 µL volume of 100 nM AP-RRE RNA was first heated to 90° C. for 5 min and then allowed to cool to, but not below, the titration temperature (37° C.). A 650 µL volume of this sample was added to the pre-thermostatted cuvette. After 10 min of temperature equilibration a solution of 5 µM M-chelate-Rev complex was titrated into the solution. After each addition, 100 µL of the solution was mixed by gentle pipeting to ensure complete mixing. The fluorescence change associated with the change of environment of the aminopurine label was monitored following peptide binding. Titration response curves were dilution and background corrected and normalized to initial intensity values. Curves were fit to a biphasic equation (4) for two independent binding sites where F$_{obs}$ is the total observed fluorescence intensity, P$_0$ is the total concentration of added M-chelate-Rev, F$_0$, F$_1$, and F$_2$ are fitting parameters corresponding to the intensities of the unbound, singly-bound, and doubly-bound AP-RNA, respectively, R$_0$ is the initial concentration of AP-RNA, and K$_{D1}$ and K$_{D2}$ are dissociation constants for binding at the high- and low-affinity sites, respectively. All binding experiments were performed in a binding buffer composed of 20 mM HEPES, 100 mM NaCl, pH 7.4.

$$F_{obs} = F_0 + \left\{ \frac{(K_{D1} + R_0 + P_0 - [((K_{D1} + R_0 + P_0)^2) - (4R_0P_0)]^{1/2})}{(2R_0) \cdot (F_1 - F_0)} \right\} + \left\{ \frac{(K_{D2} + R_0 + P_0 - [((K_{D2} + R_0 + P_0)^2) - (4R_0P_0)]^{1/2})}{(2R_0) \cdot (F_2 - F_1)} \right\}$$

PAGE Analysis of RRE RNA Cleavage Kinetics. Reactions of 100 nM metal-chelate-Rev (1:1.2 M:chelate ratio), 1 mM H$_2$O$_2$, 1 mM ascorbate, and 100 nM 5' fluorescein end-labeled RRE stem IIB RNA (F1-RNA) were conducted at 37° C. in separate tubes, each containing 20 µL total reaction volume—one tube corresponding to one gel lane. A buffer consisting of 20 mM HEPES, 100 mM NaCl, pH 7.4 was used in all experiments. F1-RNA was heated to 90° C. and allowed to cool to, but not below 37° C. prior to reaction, and the F1-RNA was immediately added to each pre-incubated tube. Reactants were added to pre-incubated tubes at time-points corresponding to the beginning of each reaction, which were performed in a dark incubator. Reaction start times were staggered and all reactions were quenched at the same time by addition of a quenching/gel-loading buffer solution (80 μL/tube) consisting of standard 1× tris-EDTA-acetic acid buffer, 8M urea, 20 mM HEPES, 100 mM NaCl. The tubes were then heated to 90° C. for 5 min and a 5 μL aliquot from each tube was then loaded into its corresponding lane of a 10% polyacrylamide 8 M urea gel, resulting in 1 pmole F1-RNA per lane. Gel electrophoresis was performed at 250 V for 1.5 h. Gels were analyzed on a GE Typhoon variable mode imager using 488 nm excitation and a 526 nm single pass emission filter. Bands were quantified with the program ImageQuant. Loss of initial F1-RNA reactant bands were fit to a first-order reaction equation using the software Origin, and observed rate constants and initial rates were determined. Control reactions with respective metal-chelates lacking the Rev domain were conducted in the same manner.

Reaction Kinetics Monitored by Real-Time Fluorimetry. Reactions of 100 nM metal-chelate-Rev (1:1.2 M:chelate ratio), 1 mM $H_2O_2$, 1 mM ascorbate, and 100 nM AP-RNA were conducted at 37° C. in a fluorescence cuvette in a Varian Cary Eclipse fluorescence spectrophotometer. Reactions were monitored using excitation at 310 nm (SW=10 nm) and emission at 371 nm (SW=10 nm). Prior to reaction the AP-RNA was pre-heated to 90° C. for 5 min and then added to the pre-warmed 37° C. cuvette. The metal-chelate-Rev complexes were added after 5 min, and reactions were initiated by the addition of $H_2O_2$ and ascorbate after an additional 10 min. Each resulting fluorescence trace was fit to a first-order reaction equation using the software Origin, and observed rate constants and initial rates were determined; the magnitude of fluorescence change that corresponded to complete reaction was established by averaging the magnitudes of fluorescence change from many trials known to react to completion. All concentrations and buffer were identical to those used in the PAGE analysis assay with F1-RNA. Control reactions with respective metal-chelates lacking the Rev domain were conducted in the same manner.

Initial rates of FI-RNA (fluorescein-labeled RNA) and AP-RNA (aminopurine-labeled RNA) cleavage and determination of dissociation constants ($K_D$) for high-affinity ($K_{D1}$) and low-affinity ($K_{D2}$) RRE RNA sites are presented in the following table. Association constants ($K_A$) are also noted.

| Complex | FI-RNA Cleavage Rate (nM/min) | AP-RNA Modification Rate (nM/min) | $K_{D1}$ (nM) | $K_{A1}$ (M$^{-1}$) × 10$^{-8}$ | $K_{D2}$ (nM) | $K_{A2}$ (M$^{-1}$) × 10$^{-8}$ |
|---|---|---|---|---|---|---|
| Cu-DOTA-Rev | 0.8 ± 0.1 | 2.8 ± 0.1 | 0.4 ± 0.1 | 25 | 488 ± 9 | 0.02 |
| Ni-DOTA-Rev | 0.009 ± 0.008 | 0.323 ± 0.004 | 2.3 ± 0.2 | 4.3 | 1180 ± 20 | 0.008 |
| Co-DOTA-Rev | 0.063 ± 0.005 | 0.332 ± 0.008 | 2.1 ± 0.2 | 4.8 | 2550 ± 40 | 0.004 |
| Fe-DOTA-Rev | 0.026 ± 0.006 | 0.367 ± 0.009 | 0.36 ± 0.08 | 27.8 | 1120 ± 20 | 0.009 |
| Cu-DTPA-Rev | 0.496 ± 0.008 | 1.25 ± 0.04 | 16 ± 2 | 0.63 | 1570 ± 80 | 0.006 |
| Ni-DTPA-Rev | 0.054 ± 0.008 | 0.169 ± 0.002 | 4.2 ± 0.3 | 2.4 | 1840 ± 20 | 0.005 |
| Co-DTPA-Rev | 0.063 ± 0.007 | 0.66 ± 0.01 | 13.7 ± 0.7 | 0.73 | 1330 ± 20 | 0.008 |
| Fe-DTPA-Rev | 0.16 ± 0.04 | 0.248 ± 0.004 | 0.7 ± 0.8 | 14.3 | 430 ± 20 | 0.023 |
| Cu-EDTA-Rev | 0.14 ± 0.03 | 0.81 ± 0.01 | 1.9 ± 0.3 | 5.3 | 1160 ± 20 | 0.009 |
| Ni-EDTA-Rev | 0.18 ± 0.05 | 0.524 ± 0.003 | 0.8 ± 0.3 | 12.5 | 520 ± 10 | 0.019 |
| Co-EDTA-Rev | 0.17 ± 0.03 | 0.328 ± 0.003 | 0.5 ± 0.3 | 20 | 560 ± 10 | 0.018 |
| Fe-EDTA-Rev | <0.02 | 0.109 ± 0.001 | 5.6 ± 0.7 | 1.8 | 630 ± 10 | 0.015 |
| Cu-GGH-Rev | 0.045 ± 0.005 | 0.4 ± 0.3 | 4.6 ± 0.5 | 25 | 363 ± 9 | 0.028 |
| Ni-GGH-Rev | 0.026 ± 0.005 | 0.58 ± 0.01 | 1.3 ± 0.3 | 7.7 | 458 ± 8 | 0.021 |
| Co-GGH-Rev | 0.003 ± 0.007 | 0.20 ± 0.01 | 3.8 ± 0.6 | 2.6 | 360 ± 10 | 0.028 |
| Cu-KGHK-Rev (SEQ ID NO: 81) | 0.060 ± 0.005 | 0.511 ± 0.003 | 1.3 ± 0.5 | 7.7 | 148 ± 5 | 0.066 |
| Ni-KGHK-Rev (SEQ ID NO: 82) | 0.043 ± 0.003 | 0.227 ± 0.006 | 3.2 ± 0.4 | 3.1 | 173 ± 3 | 0.058 |
| Co-KGHK-Rev (SEQ ID NO: 83) | 0.031 ± 0.003 | 0.257 ± 0.009 | 1.4 ± 0.4 | 7.1 | 300 ± 6 | 0.033 |
| Cu-NTA-Rev | 2.1 ± 0.2 | 4.9 ± 0.2 | 3.5 ± 0.3 | 2.9 | 857 ± 9 | 0.012 |
| Ni-NTA-Rev | 0.067 ± 0.005 | 0.78 ± 0.01 | 2.3 ± 0.1 | 4.3 | 1160 ± 10 | 0.009 |
| Co-NTA-Rev | 0.069 ± 0.003 | 0.99 ± 0.02 | 9.4 ± 0.4 | 1.1 | 1210 ± 10 | 0.008 |
| Fe-NTA-Rev | 0.031 ± 0.006 | 0.170 ± 0.001 | 7.0 ± 0.4 | 1.4 | 950 ± 10 | 0.011 |
| Background | 0.015 ± 0.005 | 0.28 ± 0.03 | | | | |

Dissociation ($K_D$) and association ($K_A$) constants, relative fluorescence units (RFU), maximal rate ($V_{max}$)

The reactivity of the metal-chelate conjugates of HIV RRE RNA targeting peptides were evaluated for activity toward DNA in the presence of ascorbate/peroxide reagents. As demonstrated below, affinities lay within the range of 10$^4$ M$^{-1}$ and 5×10$^8$ M$^{-1}$. Association and dissociation constants for binding of Ni-chelate-Rev complexes to supercoiled pUC19 plasmid DNA:

| Complex | $K_D$ (μM bp)$^a$ | $K_A$ (M$^{-1}$, bp$^{-1}$)$^a$ |
|---|---|---|
| [Ni-DOTA]$^{1-}$-Rev | 3 ± 2 | 3.33 × 10$^5$ |
| [Ni-EDTA]$^{1-}$-Rev | 1.7 ± 0.4 | 5.9 × 10$^5$ |
| [Ni-DTPA]$^{2-}$-Rev | 1.7 ± 0.4 | 5.9 × 10$^5$ |
| [Ni-NTA]$^{0}$-Rev | 3.6 ± 0.9 | 2.8 × 10$^5$ |
| [Ni-GGH]$^{0}$-Rev | 2 ± 1 | 5.0 × 10$^5$ |
| [Ni-KGHK]$^{2+}$-Rev_ (SEQ ID NO: 82) | 3.6 ± 0.3 | 2.8 × 10$^5$ |
| Rev peptide | 5 ± 2 | 2.0 × 10$^5$ |

$^a$Concentration units are μM base pairs of pUC19 plasmid DNA.

Summary of observed rate constants for consecutive DNA nicking ($k_{nick}$) and subsequent linearization ($k_{lin}$) reactions promoted by each M-chelate-Rev and M-chelate complex.

| complex | with attached Rev (M-chelate-REV) | | without attached Rev (M-chelate) | |
|---|---|---|---|---|
| | $k_{nick}$ for DNA nicking (min$^{-1}$) | $k_{lin}$ for DNA linearization (min$^{-1}$) | $k_{nick}$ for DNA nicking (min$^{-1}$) | $k_{lin}$ for DNA linearization (min$^{-1}$) |
| Fe-DOTA | 0.06 ± 0.01 | 0.0008 ± 0.0002 | —$^a$ | 0.0008 ± 0.0001 |
| Fe-DTPA | 0.025 ± 0.005 | 0.0011 ± 0.0002 | —$^a$ | 0.0012 ± 0.0001 |
| Fe-EDTA | 0.07 ± 0.02 | 0.0021 ± 0.0007 | 0.044 ± 0.009 | 0.0005 ± 0.0001 |
| Fe-NTA | 0.04 ± 0.02 | 0.002 ± 0.001 | 0.05 ± 0.01 | 0.0008 ± 0.0002 |
| Co-DOTA | 0.05 ± 0.01 | 0.0012 ± 0.0002 | —$^a$ | 0.0005 ± 0.0001 |
| Co-DTPA | 0.015 ± 0.001 | 0.0009 ± 0.0002 | —$^a$ | —$^a$ |
| Co-EDTA | 0.0177 ± 0.0008 | 0.005 ± 0.003 | 0.08 ± 0.02 | —$^a$ |
| Co-GGH | 0.037 ± 0.005 | 0.0021 ± 0.0002 | —$^a$ | <0.0002 |
| Co-KGHK (SEQ ID NO: 83) | 0.03 ± 0.01 | 0.0013 ± 0.0005 | 0.014 ± 0.002 | 0.0042 ± 0.0008 |
| Co-NTA | 0.04 ± 0.04 | 0.0010 ± 0.0007 | 0.1 ± 0.1 | 0.005 ± 0.003 |
| Ni-DOTA | 0.016 ± 0.004 | 0.0008 ± 0.0006 | 0.030 ± 0.007 | 0.0029 ± 0.0008 |
| Ni-DTPA | 0.10 ± 0.01 | 0.0021 ± 0.0007 | —$^a$ | —$^a$ |
| Ni-EDTA | 0.041 ± 0.007 | 0.0011 ± 0.0004 | 0.037 ± 0.002 | 0.00019 ± 0.00002 |
| Ni-GGH | 0.067 ± 0.008 | 0.0015 ± 0.0007 | —$^a$ | —$^a$ |
| Ni-KGHK (SEQ ID NO: 82) | 0.024 ± 0.007 | 0.0016 ± 0.0004 | —$^a$ | 0.0003 ± 0.0001 |
| Ni-NTA | 0.08 ± 0.01 | 0.0016 ± 0.0004 | —$^a$ | <0.009 |
| Cu-DOTA | 0.043 ± 0.007 | 0.0025 ± 0.0008 | —$^a$ | 0.0013 ± 0.0001 |
| Cu-DTPA | 0.11 ± 0.01 | 0.0083 ± 0.0008 | —$^a$ | —$^a$ |
| Cu-EDTA | 0.076 ± 0.005 | 0.0032 ± 0.0007 | 0.032 ± 0.003 | 0.00030 ± 0.00003 |
| Cu-GGH | 0.069 ± 0.006 | 0.0013 ± 0.0001 | 0.06 ± 0.01 | 0.0012 ± 0.0002 |
| Cu-KGHK (SEQ ID NO: 81) | 0.17 ± 0.04 | 0.0062 ± 0.0006 | 0.055 ± 0.008 | 0.00054 ± 0.00004 |
| Cu-NTA | 0.615 ± 0.006 | 0.0135 ± 0.0009 | 0.148 ± 0.007 | 0.0032 ± 0.0004 |
| Background | 0.006 ± 0.001 | 0.00024 ± 0.00003 | 0.006 ± 0.001 | 0.00024 ± 0.00003 |

$^a$Below detection limit. Concentrations used for nuclease assays are 100 nM M-chelate-Rev and 10 μM base pairs of pUC19 plasmid DNA.

In general, structural modeling of the lisinopril metallodrugs with sACE-1, and the RRE RNA-metallopeptide complexes places the reactive metal centers in close proximity (<10 Å) to the target protein or RNA, respectively. Interactions between both the N- and C-domains of sACE-1 and the M-chelate-lisinopril complexes were modeled using a combination of Spartan and Gaussian software. From the X-ray crystal structure of the N-domain of sACE-1 in complex with the inhibitor lisinopril (PDB ID: 2C6N), a sphere with 15 Å radius, centered on the N atom of the lisinopril lysine sidechain, was generated in Gaussian and used to model the active site. This process was repeated using the X-Ray crystal structure of the C-domain of ACE (tACE) in complex with lisinopril (PDB ID: 1O86). Molecular mechanics energy minimization was performed in Spartan using the Merck molecular force field MMFFaq, in which structural energy minimization occurred without solvent considerations. Model geometries were constrained to the X-Ray crystal structures, while the lisinopril lysine sidechain and lysine-chelate linker geometries were allowed to vary during energy minimization. Structures were accepted once 10 successive rounds of energy minimization lowered the energy by no more than 0.1 kcal/mol. Modeling parameters: equilibrium geometry at ground state, subject to frozen atoms and symmetry, multiplicity=singlet, total charge=0 (partial charges handled by MMFFaq).

In the case of the RRE RNA-metallopeptide complexes, these interactions were generally modeled using Spartan software. Molecular mechanics energy minimization was performed using the Merck molecular force field MMFFaq, in which structural energy minimization occurred without solvent considerations. Model geometries were constrained to the average structure of the RNA-Rev peptide complex (PDB ID: 1ETF) and M-chelate X-Ray crystal structures, while the N-terminal lysine (threonine in GGH-Rev and KGHK-Rev (SEQ ID NO: 2)) and lysine-chelate linker geometries were allowed to vary during energy minimization. Structures were accepted once 10 successive rounds of energy minimization lowered the energy by no more than 0.01 kcal/mol. Modeling parameters: equilibrium geometry at ground state, subject to frozen atoms and symmetry, multiplicity=singlet. For each complex, the total charge used during energy minimization corresponded to that expected at pH 7.4.

Example 5

Peptide Metallodrugs Targeting HCV Internal Ribosome Entry Site (IRES) RNA

Figure 6:
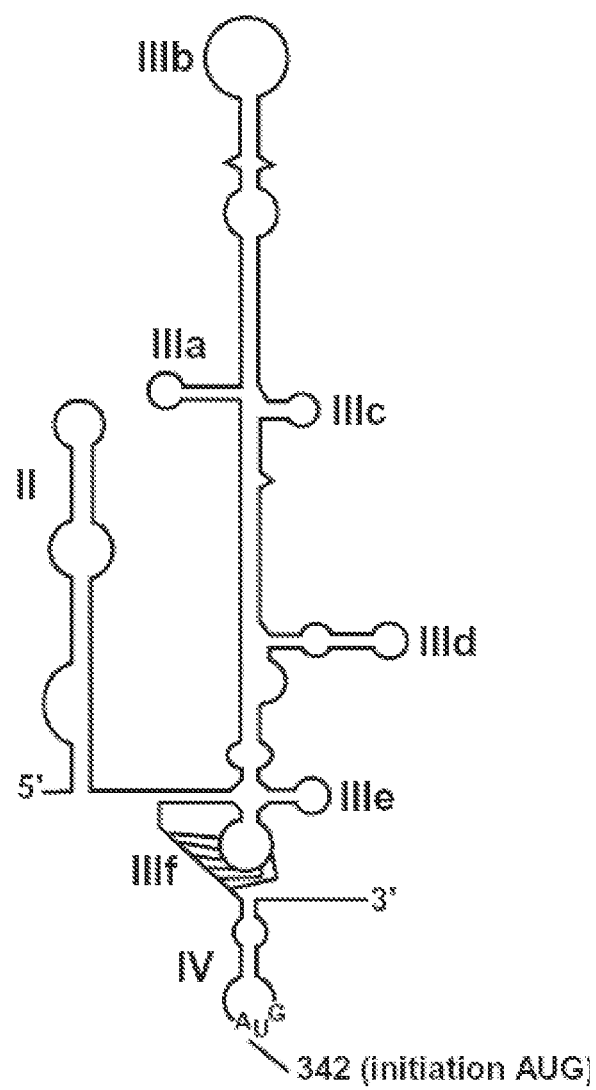
FIG. 6: The stem-loop domain structure of HCV IRES RNA.

RNA was purchased from Dharmacon, part of Thermo Fisher Scientific (Lafayette, Colo.). Peptides were purchased from Genemed Synthesis Inc (South San Francisco, Calif.) with C-terminal amidation. The stem-loop (SL) structure (from Lytle et al., RNA 13: 539-48, 2002) is depicted in FIG. 6. The sequence for the IRES SL IIb RNA used was 5'-Fluorescein-GGCAGAAAGCGUCUAGCCAUGGCG-UUAGUAUGCC-3' (SEQ ID NO: 84), and for the IRES SL IV RNA was 5'-Fluorescein-GGACCGUGCACCAUGAG-CACGAAUCC-3' (SEQ ID NO: 85). All RNA was annealed by heating to 95° C. and then cooled slowly to room temperature before use.

RNA binding experiments were performed in the presence of 84 nM GGHYrFK-amide in 20 mM HEPES (pH 7.4), 100 mM NaCl. For GGHYrFK-amide, serial additions of unlabeled IRES RNA were added and tyrosine emission was monitored ($\lambda_{ex}$=280 nm, $\lambda_{em}$=313 nm). Binding data for GGHYrFKGGGYGRKKRRQRRR-amide and GGHYrFKGGGKDEL-amide were obtained by adding serial additions of peptide to 5'-fluorescein labeled IRES SLIIb and monitoring at 518 nm (Ex=485 nm). Data was then fit to a one-site binding model.

HCV IRES RNA cleavage was monitored in vitro by fluorescence using 5' fluorescein end-labeled RNA with excitation and emission wavelengths of 485 nm and 518 nm, respectively. Reactions were carried out in reaction volumes of 100 μl in the presence of 1 mM ascorbate and 1 mM $H_2O_2$ in 20 mM HEPES buffer (pH=7.4), 100 mM NaCl with 100 nM of the catalyst and analyzed according to the change in fluorescence observed as the reaction occurred. Both a time-dependence and a concentration-dependence of RNA substrate were observed. The initial velocities were fit to a line using Origin 7.0 software and $k_{obs}$ obtained. These values were then used to obtain the Michaelis-Menten parameters.

HCV Cellular Replicon Assay. A stable cell line ET (luc-ubi-neo/ET) was employed in the assay. The ET is a Huh7 human hepatoma cell line that contains an HCV RNA replicon with a stable luciferase (Luc) reporter and three cell culture-adaptive mutations. The HCV RNA replicon antiviral evaluation assay examined the effects of compounds at six half-log concentrations each. Human interferon alpha-2b was included in each run as a positive control compound. Subconfluent cultures of the ET line were plated out into 96-well plates that were dedicated for the analysis of cell numbers (cytotoxicity) or antiviral activity, and various concentrations of metallodrugs and controls were added to the appropriate wells the following day. Cells were processed 72 h later when the cells were still sub-confluent. Six half-log serial dilutions of the compound were performed, and values derived for $IC_{50}$ (the concentration that inhibited virus replication by 50%), $TC_{50}$ (the concentration that lowered cell viability by 50%) and TI (the selectivity index: $TC_{50}/IC_{50}$). HCV RNA replicon levels were assessed as the replicon-derived Luc activity. The toxic concentration of drug that reduced cell numbers (cytotoxicity) was assessed by the CytoTox-1 cell proliferation colorimetric assay (Promega).

Exemplary IRES targeting peptides incorporate an N-terminal metal binding ATCUN motif coupled to a peptide which targets to HCV IRES RNA. The following table summarizes representatives from the various families of metallodrugs that were designed to target distinct stem-loop motifs on IRES RNA (C-terminal amidated unless otherwise noted), and pegylated forms, where PEG24 and PEG48 contain 24 and 48 ethylene units, respectively. These short peptide sequences contain a metal binding ATCUN motif (GGH, GGh, KGH, KKH) and a short peptide binding motif that recognizes stem-loop structures in domains IIB, III and IV of IRES RNA. Lower case amino acid single letter abbreviations represent D-configuration residues, and PEG represents polyethylene glycol.

```
                                            (SEQ ID NO: 10)
GGHGKYKETDLLILFKDDYFAKKNEERK (SEQ ID NO: 11)
GGHGKYKETDLLILFKDDYFAKKNEERKYGRKKRRQRRR (SEQ ID NO: 12)
GGHGKYKETDLLILFKDDYFAKKNEERKGGGYGRKKRRQRRR (SEQ ID NO: 13)
GGHKYKETDLLILFKDDYFAKKNEERKYGRKKRRQRRR (SEQ ID NO: 14)
GGHKYKETDLLILFKDDYFAKKNEERKGGGYGRKKRRQRRR (SEQ ID NO: 15)
GGHGKYKETDLLILFKDDYFAKKNEERKKDEL (SEQ ID NO: 16)
GGHGKYKETDLLILFKDDYFAKKNEERKGGGKDEL (SEQ ID NO: 17)
GGHGAALEAKICHQIEYYFGDF (SEQ ID NO: 18)
GGHAALEAKICHQIEYYFGDF

GGHGYrFK

GGHGYrFKGGGYGRKKRRQRRR

GGHGYrFKGGGKDEL

GGHYrFK

GGhyrfk

GGHYrFKGGGYGRKKRRQRRR

GGHYrFKGGGKDEL (SEQ ID NO: 10)
GGHGKYKETDLLILFKDDYFAKKNEERK

GGHYrFK-carboxylate

KKHYrFK (SEQ ID NO: 19)
GGHKYKETDLLILFKDDYFAKKNEERK (SEQ ID NO: 20)
GGHKYKETDLLILFKDDYFAKKNEERKKDEL (SEQ ID NO: 21)
GGHKYKETDL (SEQ ID NO: 21)
GGHKYKETDL (SEQ ID NO: 86)
GGHYRFK

GGHYrFKGGC-PEG24

GGHYrFKGGC-PEP48
```

A selection of metal-chelate (Cu-GGH or Cu-GGh) conjugates of HCV IRES stem-loop IIb targeting peptides were prepared and their affinity and reactivity toward the RNA motif was evaluated in the presence of ascorbate/peroxide reagents. The following table shows apparent rates of activity ($V_{max}$) for cleavage of stem loop IIb HCV IRES RNA domains by several metallopeptide derivatives incorporating a Cu-GGH or Cu-GGh metal binding domain and C-terminal RNA binding domains. Lower case amino acid single letter abbreviations represent D-configuration residues. Both dissociation and association constants are listed. Affinities lay within the range of $10^4$ $M^{-1}$ and $5\times10^8$ $M^{-1}$.

| Compound | $K_D$ (μM) | $K_A$ ($M^{-1}$) | Vmax (RFU/min) |
|---|---|---|---|
| Cu-GGHYrFK-amide | 0.044 | $2.27 \times 10^7$ | 1.71 |
| Cu-GGhyrfk-amide | 6.09 | $1.64 \times 10^5$ | 2.86 |
| Cu-GGHYRFK-amide (SEQ ID NO: 87) | 6.9 | $1.45 \times 10^5$ | 3.96 |
| Cu-GGHKYKETDL-amide (SEQ ID NO: 88) | — | — | 3.27 |

-continued

| Compound | $K_D$ (μM) | $K_A$ (M$^{-1}$) | Vmax (RFU/min) |
|---|---|---|---|
| Cu-GGHKYKETDLLILFKDDYFAKKNEERK-amide (SEQ ID NO: 89) | 1.8 | 5.56 × 10$^5$ | 13.96 |

Dissociation ($K_D$) and association ($K_A$) constants, relative fluorescence units (RFU), maximal rate ($V_{max}$) for cleavage of HCV IRES stem-loop IIb.

Dissociation ($K_D$) and association ($K_A$) constants, relative fluorescence units (RFU), maximal rate ($V_{max}$) for cleavage of HCV IRES stem-loop IIb.

Apparent rates of activity ($V_{max}$) for cleavage of stem loop IV HCV IRES RNA domains by several metallopeptide derivatives incorporating a Cu-GGH metal binding domain and C-terminal RNA binding domains are shown in the following table. Both dissociation and association constants are listed.

| Compound | KD (μM) | KA (M$^{-1}$) | Vmax (RFU/min) |
|---|---|---|---|
| Cu-GGHYRFK-amide (SEQ ID NO: 87) | 6.9 | 1.45 × 10$^5$ | 0.95 |
| Cu-GGHKYKETDLLILFKDDYFAKKNEERK-amide (SEQ ID NO: 89) | 7 | 1.43 × 10$^5$ | 2.0 |

Dissociation ($K_D$) and association ($K_A$) constants, relative fluorescence units (RFU), maximal rate ($V_{max}$).

Figure 7:
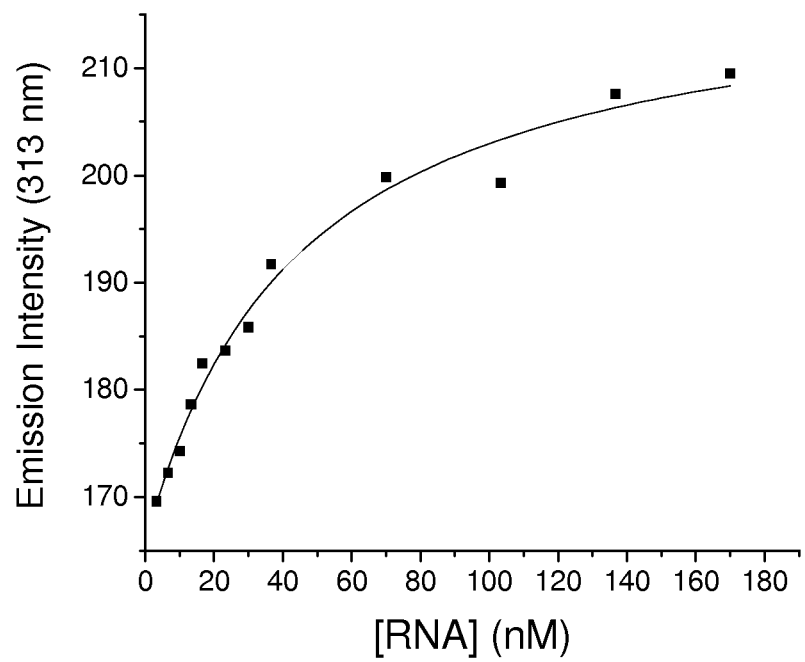
FIG. 7: (Top) Binding curve for GGHYrFK-NH$_2$ to stem-loop IIb of HCV IRES RNA. (Bottom) Michaelis-Menten plots for metallodrug Cu-GGHYrFK-NH$_2$ (square) and its D-isomer Cu-GGhyrfk-NH$_2$ (circle).
Figure 7:
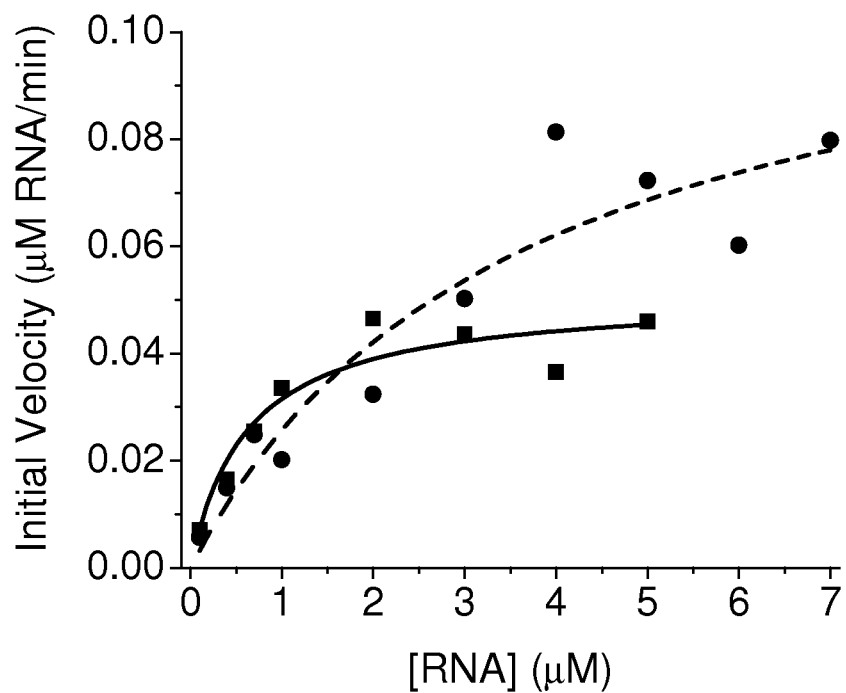

The reactivity of select catalytic metallodrugs was investigated by Michaelis-Menten profiles. Reaction chemistry was followed by monitoring the fluorescence change of 5'-fluorescein-labeled RNA as a function of time. Initial velocities were measured as a function of substrate (RNA) concentration to generate a standard Michaelis-Menten plot (FIG. 2). Metallodrug GGHYrFK, which selectively targets stem-loop IIb of the internal ribosomal entry site (IRES) RNA of hepatitis C virus (HCV) demonstrates enzyme-like turnover with a $K_M$ of 0.85 μM, $k_{cat}$ of 0.53 min$^{-1}$ and turnover number of 32; only four-fold lower $k_{cat}$ than natural ribozymes, and a $k_{cat}/K_M$ within two orders of magnitude of RNase A. While the use of BiaCore and titration calorimetry proved problematic for binding studies, monitoring the intrinsic emission from the Tyr residue on the metallodrug did prove an effective method to quantitate binding. The $K_D$ for binding of GGHYrFK to the stem loop IIb domain was determined to be 44±2 nM by monitoring the change in tyrosine emission at 313 nm following binding to the RNA (FIG. 7).

Using an HCV RNA replicon antiviral activity assay, several metallodrugs that target the domain IIB, III and IV stem loop structures on the HCV IRES RNA were tested. In addition, two pegylated forms, GGHGYrFKGGC-PEG24 and Cu-GGHGYrFKGGC-PEG48, displayed similar solution reactivity and antiviral activity, where PEG24 and PEG48 contain 24 and 48 ethylene units, respectively. The table below relates parameters for representative candidates.

| Metallodrug (SEQ ID NOS 90-96, respectively, in order of appearance) | antiviral IC$_{50}$ | cytotoxicity TC$_{50}$ | selectivity index SI$_{50}$ |
|---|---|---|---|
| Cu-GGHGKYKETDLLILFKDDYFAKKNEERK | 0.55 μM | >100 μM | >55 |
| KYKETDLLILFKDDYFAKKNEERK | >100 μM | >100 μM | 1 |
| Cu-GGHKYKETDLLILFKDDYFAKKNEERKYGRKKRRQRRR | 0.83 μM | >50 μM | >60 |
| Cu—GGHGKYKETDLLILFKDDYFAKKNEERKKDEL | 0.75 μM | >50 μM | >67 |
| AALEAKICHQIEYYFGDF | >100 μM | >100 μM | 1 |
| Cu—GGHGAALEAKICHQIEYYFGDF | 6.25 μM | 52 μM | 8.4 |
| Cu—GGHAALEAKICHQIEYYFGDF | 3.46 μM | 41.08 μM | 12 |
| Cu—GGHGYrFK | 1.38 μM | >100 μM | >72 |
| Cu—GGHGYrFKGGGYGRKKRRQRRR | 0.95 μM | 96 μM | 101 |
| Cu—GGHGYrFKGGGKDEL | 0.91 μM | >100 μM | >110 |
| Cu—GGHYrFK | 0.58 μM | >100 μM | >172 |
| YrFK | >100 μM | >100 μM | 1 |
| Cu—GGHYrFKGGGYGRKKRRQRRR | 1.85 μM | 84 μM | 62 |
| Cu—GGHGYrFKGGC-PEG24 | 2.06 μM | >50 μM | >24.3 |
| Cu—GGHGYrFKGGC-PEG48 | 1.88 μM | >50 μM | >26.6 |

Cellular antiviral activity studies were shown to be consistent with binding and cleavage chemistry by the metallodrugs. Cleavage of IRES in cell studies was confirmed by use of RT-PCR amplification experiments where the HCV replicon RNA was quantitatively measured in real time by use of 5' exonuclease reverse transcriptase using primer-probe combinations that recognize HCV IRES and were quantitated in the 'linear' phase of the reaction. Metallodrug Cu-GGHYrFK-$NH_2$ demonstrated the highest $SI_{50}$ (>172), with an antiviral activity ($IC_{50}$) of 0.58 μM and a cytotoxicity threshold exceeding 100 μM.

Example 6

Apparent binding affinities and rates of inactivation for the metalloproteinase ECE-1 protease by metallopeptide incorporating a Cu-ATCUN metal binding domain and C-terminal protease binding domains.

| | $K_A$ ($M^{-1}$) | $k_{inact}$ ($min^{-1}$) |
|---|---|---|
| Cu—GGHGGDF (SEQ ID NO: 97) | 8 × $10^4$ | 0.5 |

Example 7

Apparent binding affinities and rates of inactivation for HCV protease by several metallopeptide derivatives incorporating a Cu-GGH metal binding domain and C-terminal HCV protease targeting peptides were prepared and their affinity and reactivity were evaluated under in the presence of various redox reagents. Affinities lay within the range of $10^4$ $M^{-1}$ and $5\times10^8$ $M^{-1}$.

| | $K_A$ ($M^{-1}$) | $k_{inact}$ ($min^{-1}$) |
|---|---|---|
| Cu—GGHGDEMEEC (SEQ ID NO: 98) | 4.8 × $10^4$ | 0.04 |
| Cu—GGHGDLEVVT (SEQ ID NO: 99) | 7.7 × $10^4$ | 0.016 |
| Cu—GGHGDeLI(Cha)T | 3.3 × $10^4$ | 0.042 |
| Cu—GGHGDeLI(Cha)C—$CO_2^-$ | 2.0 × $10^6$ | 0.0014 |
| Cu—GGHGDEMEEC—$CO_2^-$ (SEQ ID NO: 100) | 2.1 × $10^4$ | 0.0093 |

Higher affinity ligands, such as Cu-GGHGDeLI(Cha)C—$CO_2^-$ complex, which shows relatively high affinity binding to the HCV protease ($K_A$~$2\times10^6$ $M^{-1}$), exhibit relatively poor catalytic efficiency, with lower rate constant for inactivation reflecting the rate-limiting release of catalyst from the modified protease. Activity generally increases with decreasing affinity, although other factors (steric, electronic, positioning of metal associated reactive oxygen species to scissile bonds) also play an increasingly important role in dictating activity, emphasizing the point that higher affinity binding does not in itself promote efficient reactivity Example 8

Targeting *B. anthracis* Lethal Factor

Apparent binding affinities and rates of inactivation for *B. anthracis* lethal factor by several metallopeptide derivatives and a copper bound captopril-cyclam conjugate were evaluated. The copper complex of a copper bound captopril-cyclam conjugate (Cu-capclam) was also evaluated. Affinities lay within the range of $10^4$$M^{-1}$ and $5\times10^8$ $M^{-1}$.

| | $K_A$ ($M^{-1}$) | $k_{inact}$ ($min^{-1}$) |
|---|---|---|
| Cu—KGHK (SEQ ID NO: 81) | 1.25 × $10^5$ | 0.035 |
| Cu—GCHP (SEQ ID NO: 101) | 4.5 × $10^4$ | 0.077 |
| Cu—capclam | 4.5 × $10^7$ | 0.0056 |

Example 9

Targeting *S. aureus* Sortase A

Apparent binding affinities and rates of inactivation for *S. aureus* sortase A by several metallopeptide derivatives were evaluated. Affinities (IC50's) lay within the range of $10^4$ $M^{-1}$ and $5\times10^8$ $M^{-1}$.

| | IC50 | activity for catalyst concentration of 1 μM |
|---|---|---|
| Cu—GGHLPET (SEQ ID NO: 102) | >100 μM | 0.009 |
| Cu—GGHLPETG (SEQ ID NO: 103) | >100 μM | 0.017 |
| Cu—GGHGLPET (SEQ ID NO: 104) | >100 μM | 0.027 |
| Cu—GGHGLPETG (SEQ ID NO: 105) | >100 μM | 0.012 |

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A compound for catalytically inactivating a biochemical target of interest, comprising:
   a ligand moiety which binds to the biochemical target; and
   a metal binding moiety,
   wherein the ligand moiety is heterologous to the metal binding moiety, wherein the ligand moiety and the metal binding moiety are covalently linked, wherein the compound binds to the biochemical target with an affinity of between about $10^4$ $M^{-1}$ and about $0.7\times10^7$ $M^{-1}$, and wherein the compound has an off rate ($k_{off}$) for its target which is similar to that for the catalytic turnover ($k_{cat}$) of the metal binding moiety.

2. The compound according to claim 1, wherein the metal binding moiety comprises a metal bound thereto, wherein said metal is redox-active in the bound state under oxidative conditions to generate one or more reactive oxygen species.

3. The compound according to claim 1, wherein the metal binding moiety has a metal bound thereto, wherein said metal is active as a Lewis acid catalyst in the bound state under hydrolytic conditions.

4. The compound according to claim 1, wherein the metal binding moiety comprises a metal bound thereto, wherein said metal is a cation of a metal selected from the group consisting of an alkaline earth metals, metals which give rise to cations with an incomplete d sub-shell, lanthanide and actinide metals.

5. The compound according to claim 4, wherein the metal which gives rise to cations with an incomplete d-subshell is selected from the group consisting of Cu(II), Cu(III), Ni(II), Ni(III), Zn(II), Fe(II), Fe(III), Co(II), Co(III), Cr(II), and Cr(III), and other second and third row transition metal ions, and non-transition metals such as Al(III).

6. The compound according to claim 1, wherein the ligand moiety comprises a peptide or protein backbone, or pegylated form thereof.

7. The compound according to claim 1, wherein the ligand moiety comprises a carbohydrate backbone, or pegylated form thereof.

8. The compound according to claim 1, wherein the ligand moiety comprises a secondary metabolite, or pegylated form thereof.

9. The compound according to claim 1, wherein the ligand moiety comprises a nucleic acid backbone, or pegylated form thereof.

10. The compound according to claim 1, wherein the ligand moiety comprises a protein nucleic acid backbone, or pegylated form thereof.

11. The compound according to claim 1, wherein the ligand moiety comprises an organic molecular motif selected from the group consisting of an aptamer, a small organic molecule, a peptidomimetic, a dendrimer, an antibiotic, a secondary metabolite, and an antibody (or antibody fragment), or pegylated form thereof.

12. The compound according to claim 1, wherein the metal binding moiety comprises an organic chelating ligand.

13. The compound according to claim 12, wherein said organic chelating ligand coordinates a metal using amine and carboxylate functionalities on the organic chelating ligand.

14. The compound according to claim 12, wherein said organic chelating ligand coordinates a metal using the coordination chemistry of a compound selected from the group consisting of diethylenetriaminepentaacetic acid (DTPA), ethylenediamine tetraacetic acid (EDTA), N,N-bis(carboxymethyl)glycine (NTA), diethylenetriaminepentaacetate (DTPA), 1,4,7,10-tetraazacyclododecane-1,4,7,10-tetraacetic acid (DOTA), Mercaptoacetylglycine (MAG3), 1,4,8,11-Tetraazacyclotetradecane (CYCLAM), 1,4,7,10-tetraazacyclododecane, cyclen, 1,4,7-triazacyclononane (TACN), and hydrazinonicotinamide (HYNIC).

15. The compound according to claim 1, wherein the metal binding moiety comprises a peptide chelating ligand.

16. The compound according to claim 15, wherein said peptide chelating ligand coordinates a metal using terminal amine and/or amino acid sidechains, and/or deprotonated backbone amide, and/or backbone carbonyl functionalities on the peptide chelating ligand.

17. The compound according to claim 15, wherein said peptide chelating ligand is an ATCUN motif.

18. The compound according to claim 1, wherein the biochemical target is selected from the group consisting of a bacterial component, a viral component, a fungal component, a mammalian cellular component, a protozoan component, a serum component, an extracellular matrix component, a cancer cell component, and a pathogen-derived toxin.

19. The compound according to claim 1, wherein the biochemical target is a cellular or serum component selected from the group consisting of a cell receptor, a cytokine, a hormone, an enzyme, and a misfolded or polymeric form of a naturally occurring molecule.

20. The compound according to claim 1, wherein when the composition is bound to the biochemical target, the metal binding moiety is within 20 nm of the biochemical target.

21. A method of improving the efficacy of a current or candidate therapeutic molecule which is a ligand to a biochemical target, comprising: covalently conjugating said current or candidate therapeutic molecule and which lacks a metal-binding domain, to a metal binding moiety to provide a compound of claim 1, wherein the compound binds to the biochemical target with an affinity of between about $10^4$ $M^{-1}$ and about $0.7\times10^7$ $M^{-1}$, and wherein the compound has an off rate ($k_{off}$) for its target which is similar to that for the catalytic turnover ($k_{cat}$) of the metal binding moiety.

22. A method according to claim 21, wherein the metal binding moiety comprises a metal bound thereto, wherein said metal is redox-active in the bound state under oxidative conditions to generate one or more reactive oxygen species.

23. A method according to claim 21, wherein the metal binding moiety has a metal bound thereto, wherein said metal is active as a Lewis acid catalyst in the bound state under hydrolytic conditions.

24. A method for catalytically inactivating a biochemical target of interest, comprising:
contacting the biochemical target of interest with the compound according to claim 1 under conditions wherein the composition binds to, and generates reactive oxygen species proximate to, the biochemical target, wherein the concentration of reactive oxygen species generated conformationally and/or functionally alters the biochemical target, thereby inactivating the biochemical target.

25. The method according to claim 24, wherein the metal binding moiety has a metal bound thereto, wherein said metal is active as a Lewis acid catalyst in the bound state under hydrolytic conditions.

26. The method according to claim 24, wherein the metal binding moiety comprises a metal bound thereto, wherein said metal is a cation of a metal selected from the group consisting of an alkaline earth metals, metals which give rise to cations with an incomplete d sub-shell, and actinide metals.

27. A method according to claim 26, wherein the transition metal is selected from the group consisting of Cu(II), Cu(III), Ni(II), Ni(III), Zn(II), Fe(II), Fe(III), Co(II), Co(III), Cr(II), and Cr(III), and other second and third row transition metal ions, and non-transition metals such as Al(III).

28. A method according to claim 21, wherein the ligand moiety comprises a peptide or protein backbone, or pegylated form thereof.

29. A method according to claim 21, wherein the ligand moiety comprises a carbohydrate backbone, or pegylated form thereof.

30. A method according to claim 21, wherein the ligand moiety comprises a secondary metabolite, or pegylated form thereof.

31. A method according to claim 21, wherein the ligand moiety comprises a nucleic acid backbone, or pegylated form thereof.

32. A method according to claim 21, wherein the ligand moiety comprises a protein nucleic acid backbone, or pegylated form thereof.

33. A method according to claim 21, wherein the ligand moiety comprises an organic molecular motif selected from the group consisting of an aptamer, a small organic molecule, a peptidomimetic, a dendrimer, an antibiotic, a secondary metabolite, and an antibody, or pegylated form thereof.

34. A method according to claim 21, wherein the metal binding moiety comprises an organic chelating ligand.

35. A method according to claim 34, wherein said organic chelating ligand coordinates a metal using amine and carboxylate functionalities on the organic chelating ligand.

36. A method according to claim 34, wherein said organic chelating ligand coordinates a metal using the coordination chemistry of a compound selected from the group consisting of diethylenetriaminepentaacetic acid (DTPA), ethylenediamine tetraacetic acid (EDTA), N,N-bis(carboxymethyl)glycine (NTA), diethylenetriaminepentaacetate (DTPA), 1,4,7,10-tetraazacyclododecane-1,4,7,10-tetraacetic acid (DOTA), Mercaptoacetylglycine (MAG3), 1,4,8,11-Tetraazacyclotetradecane (CYCLAM), 1,4,7,10-tetraazacyclododecane, cyclen, 1,4,7-triazacyclononane (TACN), and hydrazinonicotinamide (HYNIC).

37. A method according to claim 21, wherein the metal binding moiety comprises a peptide chelating ligand.

38. A method according to claim 37, wherein said peptide chelating ligand coordinates a metal using terminal amine and/or amino acid sidechains, and/or deprotonated backbone amide, and/or backbone carbonyl functionalities on the peptide chelating ligand.

39. A method according to claim 37, wherein said peptide chelating ligand is an ATCUN motif.

40. A method according to claim 21, wherein the biochemical target is selected from the group consisting of a bacterial component, a viral component, a fungal component, a human cellular component, a protozoan component, a serum component, an extracellular matrix component, a cancer cell component, and a pathogen-derived toxin.

41. A method according to claim 21, wherein the biochemical target is a cellular or serum component selected from the group consisting of a cell receptor, a cytokine, a hormone, an enzyme, and a misfolded or polymeric form of a naturally occurring molecule.

42. A method according to claim 21, wherein when the composition is bound to the biochemical target, the metal binding moiety is within 20 nm, and preferably within 20 Å, of the biochemical target.

43. A method for therapeutically inactivating a biochemical target, comprising:
administering to a subject in need thereof the compound according to claim 1 under conditions wherein the composition binds to, and generates reactive oxygen species proximate to, the biochemical target, wherein the concentration of reactive oxygen species generated conformationally and/or functionally alters the biochemical target to therapeutic effect.

44. A method according to claim 43, administering to a subject in need thereof the compound according to claim 1 under conditions wherein the compound binds to the biochemical target, and is active as a Lewis acid catalyst in the bound state under hydrolytic conditions.

* * * * *

```
                        SEQUENCE LISTING

<160> NUMBER OF SEQ ID NOS: 106

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 1

Gly Gly His Gly Asp Glu Met Glu Glu Cys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Gly His Lys
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ile His Asn
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ile His Pro Phe
1               5

<210> SEQ ID NO 5
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 5

Pro His Gly Gly Gly Trp Gly Gln
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Gly Gly Gly
1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Gly Gly Gly Gly
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Gly Gly Cys
1

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Tyr Ala Cys Ala Ala Cys Ala Ala Ala Phe Ala Ala Lys Ala Ala
1               5                   10                  15

Leu Ala Ala His Ala Ala Ala His Ala Lys
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 10
```

```
Gly Gly His Gly Lys Tyr Lys Glu Thr Asp Leu Leu Ile Leu Phe Lys
1               5                   10                  15

Asp Asp Tyr Phe Ala Lys Lys Asn Glu Glu Arg Lys
            20                  25
```

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 11

```
Gly Gly His Gly Lys Tyr Lys Glu Thr Asp Leu Leu Ile Leu Phe Lys
1               5                   10                  15

Asp Asp Tyr Phe Ala Lys Lys Asn Glu Glu Arg Lys Tyr Gly Arg Lys
            20                  25                  30

Lys Arg Arg Gln Arg Arg Arg
        35
```

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 12

```
Gly Gly His Gly Lys Tyr Lys Glu Thr Asp Leu Leu Ile Leu Phe Lys
1               5                   10                  15

Asp Asp Tyr Phe Ala Lys Lys Asn Glu Glu Arg Lys Gly Gly Gly Tyr
            20                  25                  30

Gly Arg Lys Lys Arg Arg Gln Arg Arg Arg
        35                  40
```

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 13

```
Gly Gly His Lys Tyr Lys Glu Thr Asp Leu Leu Ile Leu Phe Lys Asp
1               5                   10                  15

Asp Tyr Phe Ala Lys Lys Asn Glu Glu Arg Lys Tyr Gly Arg Lys Lys
            20                  25                  30

Arg Arg Gln Arg Arg Arg
        35
```

<210> SEQ ID NO 14
<211> LENGTH: 41
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<223> OTHER INFORMATION: C-term amidated

<400> SEQUENCE: 14

Gly Gly His Lys Tyr Lys Glu Thr Asp Leu Leu Ile Leu Phe Lys Asp
1               5                   10                  15

Asp Tyr Phe Ala Lys Lys Asn Glu Glu Arg Lys Gly Gly Tyr Gly
            20                  25                  30

Arg Lys Lys Arg Arg Gln Arg Arg
        35                  40

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 15

Gly Gly His Gly Lys Tyr Lys Glu Thr Asp Leu Leu Ile Leu Phe Lys
1               5                   10                  15

Asp Asp Tyr Phe Ala Lys Lys Asn Glu Glu Arg Lys Lys Asp Glu Leu
            20                  25                  30

<210> SEQ ID NO 16
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 16

Gly Gly His Gly Lys Tyr Lys Glu Thr Asp Leu Leu Ile Leu Phe Lys
1               5                   10                  15

Asp Asp Tyr Phe Ala Lys Lys Asn Glu Glu Arg Lys Gly Gly Gly Lys
            20                  25                  30

Asp Glu Leu
        35

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 17

Gly Gly His Gly Ala Ala Leu Glu Ala Lys Ile Cys His Gln Ile Glu
1               5                   10                  15

Tyr Tyr Phe Gly Asp Phe
            20

<210> SEQ ID NO 18
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 18

Gly Gly His Ala Ala Leu Glu Ala Lys Ile Cys His Gln Ile Glu Tyr
1               5                   10                  15

Tyr Phe Gly Asp Phe
            20

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 19

Gly Gly His Lys Tyr Lys Glu Thr Asp Leu Leu Ile Leu Phe Lys Asp
1               5                   10                  15

Asp Tyr Phe Ala Lys Lys Asn Glu Glu Arg Lys
            20                  25

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 20

Gly Gly His Lys Tyr Lys Glu Thr Asp Leu Leu Ile Leu Phe Lys Asp
1               5                   10                  15

Asp Tyr Phe Ala Lys Lys Asn Glu Glu Arg Lys Lys Asp Glu Leu
            20                  25                  30

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 21

Gly Gly His Lys Tyr Lys Glu Thr Asp Leu
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: C-term amidated

<400> SEQUENCE: 22

Gly Gly His Lys Tyr Lys Glu Thr Asp Leu
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 23

Gly Gly His Tyr Arg Phe Lys
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 24

Gly Gly His Gly Asp Glu Met Glu Glu Cys Ala Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly His Gly Asp Glu Met Glu Glu Cys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 26

Gly Gly His Gly Asp Glu Met Glu Glu Cys
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

```
<400> SEQUENCE: 27

Gly Gly His Gly Asp Glu Met Glu Glu Cys Ala Ser Tyr Ser Lys Asp
1               5                   10                  15

Glu Leu

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 28

Gly Gly His Gly Asp Leu Glu Val Val Thr
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 29

Gly Gly His Gly Asp Leu Glu Val Val Thr Ala Ser Tyr Ser Lys Asp
1               5                   10                  15

Glu Leu

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 30

Gly Gly His Gly Ala Arg Val Leu Ala Glu Ala Met
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 31

Gly Gly His Val Leu Gln Asn Tyr Pro Ile Val Gln
1               5                   10

<210> SEQ ID NO 32
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 32

Gly Gly His Gly Ala Glu Val Phe Tyr Val Asp Gly Ala
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 33

Gly Gly His Thr Arg Gln Ala Arg Arg Asn Arg Arg Arg Trp Arg
1               5                   10                  15

Glu Arg Gln Arg
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 34

Lys Gly His Lys Thr Arg Gln Ala Arg Arg Asn Arg Arg Arg Trp
1               5                   10                  15

Arg Glu Arg Gln Arg
            20

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 35

Gly Gly His Gly Phe Thr Thr Lys Ala Leu Gly Ile Ser Tyr Gly Arg
1               5                   10                  15

Lys Lys Arg Arg Gln Arg Arg Arg Pro Pro Gln Gly Ser Gln Thr His
            20                  25                  30

Gln Val Ser Leu Ser Lys Gln
            35

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: C-term amidated

<400> SEQUENCE: 36

Gly Gly His Phe Thr Thr Lys Ala Leu Gly Ile Ser Tyr Gly Arg Lys
1               5                   10                  15
Lys Arg Arg Gln Arg Arg Arg Pro Pro Gln Gly Ser Gln Thr His Gln
            20                  25                  30
Val Ser Leu Ser Lys Gln
        35

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 37

Gly Gly His Gly Arg Arg Arg Asp Arg Arg Leu Arg Gln Arg Ala Arg
1               5                   10                  15
Arg Arg

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 38

Gly Gly His Leu Pro Glu Thr Gly
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 39

Gly Gly His Gly Leu Pro Glu Thr Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 40

Gly Gly His Leu Pro Glu Thr
1               5
```

```
<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 41

Gly Gly His Gly Leu Pro Glu Thr
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly His Leu Pro Glu Thr
1               5

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 43

Gly Gly His Ile Lys Asn Tyr Pro Ala Arg Val Lys Cys
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 44

Gly Gly His Val Ser Gln Phe Pro Ala Arg Ile Lys Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 45

Gly Gly His Val Ser Gln Phe Pro Ala Arg Ile Lys
1               5                   10
```

```
<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 46

Gly Gly His Leu Ser Leu Pro Pro Val Lys Leu His Ser
1               5                   10

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 47

Gly Gly His Gly Gln Arg Lys Leu Phe Phe Asn Leu Arg Lys Thr Lys
1               5                   10                  15

Gln Arg Leu Gly Trp Phe Asn Gln Cys
            20                  25

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 48

Gly Gly His Gly Glu Tyr Val Leu Arg Asn Trp Arg Ile Val Lys Val
1               5                   10                  15

Ala Thr Thr Lys Ala Cys
            20

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 49

Gly Gly His Gly Gly Cys His Pro
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: C-term amidated

<400> SEQUENCE: 50

Gly Gly His Gly Gly Asp His Pro
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 51

Gly Gly His Gly Ile Glu Pro
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 52

Gly Gly His Gly Ile Lys Tyr
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 53

Gly Gly His Gly Ile Lys Trp
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 54

Gly Gly His Gly Ile Lys Pro
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: C-term amidated

<400> SEQUENCE: 55

Gly Gly His Gly Gly Asp Phe
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 56

Gly Gly His Gly Gly Asp Tyr
1               5

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 57

Gly Gly His Arg Ala Gly Leu Gln Phe Pro Val Gly Arg Val His Arg
1               5                   10                  15

Leu Leu Arg Lys
            20

<210> SEQ ID NO 58
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 58

Gly Gly His Thr Arg Ser Ser Arg Ala Gly Leu Gln Phe Pro Val Gly
1               5                   10                  15

Arg Val His Arg Leu Leu Arg Lys
            20

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 59

Gly Gly His Gly Ile Arg Arg Ile Ile Arg Lys Ile Ile His Ile Ile
1               5                   10                  15

Lys Lys
```

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 60

Gly Gly His Gly Val Arg Arg Phe Pro Trp Trp Trp Pro Phe Leu Arg
1               5                   10                  15

Arg

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 61

Gly Gly His Gly Ile Leu Ala Trp Lys Trp Ala Trp Trp Ala Trp Arg
1               5                   10                  15

Arg

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 62

Gly Gly His Gly Arg Leu Ala Arg Ile Val Val Ile Arg Val Ala Arg
1               5                   10                  15

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 63

Gly Gly His Gly Gly Leu Phe Asp Ile Ile Lys Lys Ile Ala Glu Ser
1               5                   10                  15

Ile

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: C-term amidated

<400> SEQUENCE: 64

Gly Gly His His Pro Val His His Tyr Gln
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 65

Gly Gly His Gly His Pro Val His His Tyr Gln
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 66

Gly Gly His Gly Gly His Pro Val His His Tyr Gln
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 67

Gly Gly His Gly Leu Pro Leu Thr Pro Leu Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 68

Gly Gly His Gly Gly Leu Pro Leu Thr Pro Leu Pro
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
<220> FEATURE:
<223> OTHER INFORMATION: C-term amidated

<400> SEQUENCE: 69

Gly Gly His Gly Trp Arg Trp Tyr Cys Arg
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 70

Gly Gly His Gly Gly Trp Arg Trp Tyr Cys Arg
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly His Asp Glu Met Glu Glu Cys
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Asp Ile Val Pro Cys
1               5

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 73

Gly Gly His Thr Arg Ser Ser Arg Ala Gly Leu Gln Phe Pro Val Gly
1               5                   10                  15

Arg Val His Arg Leu Leu Arg Lys
            20

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: N-term Mca
<220> FEATURE:
<221> NAME/KEY: MOD_RES
<222> LOCATION: (9)..(9)
<223> OTHER INFORMATION: Lys-Dnp-OH

<400> SEQUENCE: 74

Arg Pro Pro Gly Phe Ser Ala Phe Lys
1               5

<210> SEQ ID NO 75
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: 2-amino purine

<400> SEQUENCE: 75
ggucugggcg cagcgcaagc ugacggnaca ggcc                                34

<210> SEQ ID NO 76
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Fluorescein

<400> SEQUENCE: 76
uuggucuggg cgcagcgcaa gcugacggua caggcc                              36

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 77

Lys Thr Arg Gln Ala Arg Arg Asn Arg Arg Arg Trp Arg Glu Arg
1               5                   10                  15

Gln Arg

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 78

Gly Gly His Thr Arg Gln Ala Arg Arg Asn Arg Arg Arg Arg Trp Arg

```
                1               5                   10                  15
Glu Arg Gln Arg
            20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 79

Lys Gly His Lys Thr Arg Gln Ala Arg Arg Asn Arg Arg Arg Trp
1               5                   10                  15

Arg Glu Arg Gln Arg
            20

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 80

Lys Gly His Lys
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 81

Lys Gly His Lys
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ni

<400> SEQUENCE: 82

Lys Gly His Lys
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                        peptide
<220> FEATURE:
<223> OTHER INFORMATION: N-term Co

<400> SEQUENCE: 83

Lys Gly His Lys
1

<210> SEQ ID NO 84
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Fluorescein

<400> SEQUENCE: 84
ggcagaaagc gucuagccau ggcguuagua ugcc                               34

<210> SEQ ID NO 85
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Fluorescein

<400> SEQUENCE: 85
ggaccgugca ccaugagcac gaaucc                                        26

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 86

Gly Gly His Tyr Arg Phe Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu
<220> FEATURE:
<223> OTHER INFORMATION: C-term amidated

<400> SEQUENCE: 87

Gly Gly His Tyr Arg Phe Lys
1               5

<210> SEQ ID NO 88
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Cu
<220> FEATURE:
<223> OTHER INFORMATION: C-term amidated

<400> SEQUENCE: 88

Gly Gly His Lys Tyr Lys Glu Thr Asp Leu
1               5                   10

<210> SEQ ID NO 89
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu
<220> FEATURE:
<223> OTHER INFORMATION: C-term amidated

<400> SEQUENCE: 89

Gly Gly His Lys Tyr Lys Glu Thr Asp Leu Leu Ile Leu Phe Lys Asp
1               5                   10                  15

Asp Tyr Phe Ala Lys Lys Asn Glu Glu Arg Lys
            20                  25

<210> SEQ ID NO 90
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 90

Gly Gly His Gly Lys Tyr Lys Glu Thr Asp Leu Leu Ile Leu Phe Lys
1               5                   10                  15

Asp Asp Tyr Phe Ala Lys Lys Asn Glu Glu Arg Lys
            20                  25

<210> SEQ ID NO 91
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Tyr Lys Glu Thr Asp Leu Leu Ile Leu Phe Lys Asp Asp Tyr Phe
1               5                   10                  15

Ala Lys Lys Asn Glu Glu Arg Lys
            20

<210> SEQ ID NO 92
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Cu
```

<400> SEQUENCE: 92

Gly Gly His Lys Tyr Lys Glu Thr Asp Leu Leu Ile Leu Phe Lys Asp
1               5                   10                  15

Asp Tyr Phe Ala Lys Lys Asn Glu Glu Arg Lys Tyr Gly Lys Lys
            20                  25                  30

Arg Arg Gln Arg Arg Arg
        35

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Cu

<400> SEQUENCE: 93

Gly Gly His Gly Lys Tyr Lys Glu Thr Asp Leu Leu Ile Leu Phe Lys
1               5                   10                  15

Asp Asp Tyr Phe Ala Lys Lys Asn Glu Glu Arg Lys Lys Asp Glu Leu
            20                  25                  30

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ala Leu Glu Ala Lys Ile Cys His Gln Ile Glu Tyr Tyr Phe Gly
1               5                   10                  15

Asp Phe

<210> SEQ ID NO 95
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 95

Gly Gly His Gly Ala Ala Leu Glu Ala Lys Ile Cys His Gln Ile Glu
1               5                   10                  15

Tyr Tyr Phe Gly Asp Phe
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 96

```
Gly Gly His Ala Ala Leu Glu Ala Lys Ile Cys His Gln Ile Glu Tyr
1               5                   10                  15

Tyr Phe Gly Asp Phe
            20

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 97

Gly Gly His Gly Gly Asp Phe
1               5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 98

Gly Gly His Gly Asp Glu Met Glu Glu Cys
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 99

Gly Gly His Gly Asp Leu Glu Val Val Thr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu
<220> FEATURE:
<223> OTHER INFORMATION: C-term CO2

<400> SEQUENCE: 100

Gly Gly His Gly Asp Glu Met Glu Glu Cys
1               5                   10

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: N-term Cu

<400> SEQUENCE: 101

Gly Cys His Pro
1

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 102

Gly Gly His Leu Pro Glu Thr
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 103

Gly Gly His Leu Pro Glu Thr Gly
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 104

Gly Gly His Gly Leu Pro Glu Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cu

<400> SEQUENCE: 105

Gly Gly His Gly Leu Pro Glu Thr Gly
1               5

<210> SEQ ID NO 106
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term metallic modified

<400> SEQUENCE: 106

Lys Gly His Lys
1
```